(12) United States Patent
Young et al.

(10) Patent No.: US 11,439,345 B2
(45) Date of Patent: Sep. 13, 2022

(54) METHOD AND APPARATUS FOR MONITORING VITAL SIGNS REMOTELY

(71) Applicant: Sleep Number Corporation, Minneapolis, MN (US)

(72) Inventors: Steven Jay Young, Los Gatos, CA (US); William McKinnon Gillon, San Mateo, CA (US); Richard Vincent Rifredi, Los Gatos, CA (US); William Todd Krein, San Jose, CA (US)

(73) Assignee: Sleep Number Corporation, Minneapolis, MN (US)

( * ) Notice: Subject to any disclaimer, the term of this patent is extended or adjusted under 35 U.S.C. 154(b) by 557 days.

(21) Appl. No.: 16/027,528

(22) Filed: Jul. 5, 2018

(65) Prior Publication Data

US 2019/0069840 A1 Mar. 7, 2019

Related U.S. Application Data

(60) Continuation of application No. 15/349,406, filed on Nov. 11, 2016, now abandoned, which is a division of
(Continued)

(51) Int. Cl.
*A61B 5/0205* (2006.01)
*A61B 5/00* (2006.01)
(Continued)

(52) U.S. Cl.
CPC .......... *A61B 5/4818* (2013.01); *A61B 5/0022* (2013.01); *A61B 5/0077* (2013.01); *A61B 5/0205* (2013.01); *A61B 5/1102* (2013.01); *A61B 5/4836* (2013.01); *A61B 5/6887* (2013.01); *A61B 5/725* (2013.01); *A61B 5/746* (2013.01); *A61B 7/003* (2013.01); *A61F 5/56* (2013.01); *G01L 19/0007* (2013.01);
(Continued)

(58) Field of Classification Search
CPC .................... A61B 5/11; A61B 5/1102; A61B 5/113–1135; A61B 2562/168; A61B 5/721–7214
See application file for complete search history.

(56) References Cited

U.S. PATENT DOCUMENTS 3,465,747 A 9/1969 Rogallo
3,481,324 A 12/1969 Talbot et al.
(Continued)

FOREIGN PATENT DOCUMENTS

CN 101954143 1/2011
JP 2004-049838 2/2004
(Continued)

OTHER PUBLICATIONS http:/fwww.lutron.com/CS1-Specs/specs/dMicrowatt.htm; "Digital MicroWA TI Lighting Automation System".

*Primary Examiner* — Meredith Weare
(74) *Attorney, Agent, or Firm* — Fish & Richardson P.C.

(57) ABSTRACT

A method and apparatus for monitoring vital signs, such as cardiopulmonary activity, using a ballistograph are provided. The method and apparatus may be used to monitor an infant sleeping in a crib, a patient in a hospital, a person with a chronic disease at home or in professional care, or a person in an elder-care setting.

14 Claims, 16 Drawing Sheets

Related U.S. Application Data application No. 11/849,051, filed on Aug. 31, 2007, now abandoned.

(60) Provisional application No. 60/846,642, filed on Sep. 22, 2006.

(51) Int. Cl.

| | | |
|---|---|---|
| *A61B 5/11* | (2006.01) | |
| *G01L 19/00* | (2006.01) | |
| *G01L 19/08* | (2006.01) | |
| *G16H 40/67* | (2018.01) | |
| *A61B 7/00* | (2006.01) | |
| *A61F 5/56* | (2006.01) | |
| *G16H 50/30* | (2018.01) | |

(52) U.S. Cl.
CPC ............ *G01L 19/08* (2013.01); *G16H 40/67* (2018.01); *G16H 50/30* (2018.01); *A61B 2503/04* (2013.01); *A61B 2505/07* (2013.01); *A61B 2562/0261* (2013.01)

(56) References Cited

U.S. PATENT DOCUMENTS

| | | |
|---|---|---|
| 3,727,606 A | 4/1973 | Sielaff |
| 3,831,596 A | 8/1974 | Cavallo |
| 3,980,076 A | 9/1976 | Wikswo, Jr. et al. |
| 4,088,138 A | 5/1978 | Diack et al. |
| 4,146,885 A | 3/1979 | Lawson, Jr. |
| 4,195,643 A | 4/1980 | Pratt, Jr. |
| 4,299,233 A | 11/1981 | Lemelson |
| 4,438,771 A | 3/1984 | Friesen et al. |
| 4,494,553 A | 1/1985 | Sciarra et al. |
| 4,648,396 A | 3/1987 | Raemer |
| 4,657,025 A | 4/1987 | Orlando |
| 4,657,026 A | 4/1987 | Tagg |
| 4,662,012 A | 5/1987 | Tarbet |
| 4,679,569 A * | 7/1987 | Lee ................ A61B 5/1102 128/870 |
| 4,681,098 A | 7/1987 | Lee |
| 4,738,266 A | 4/1988 | Thatcher |
| 4,766,628 A | 8/1988 | Walker |
| 4,788,533 A | 11/1988 | Mequignon |
| 4,788,729 A | 12/1988 | Walker |
| 4,817,610 A | 4/1989 | Lee |
| 4,829,616 A | 5/1989 | Walker |
| 4,836,215 A | 6/1989 | Lee |
| 4,838,275 A | 6/1989 | Lee |
| 4,848,350 A | 7/1989 | Lee |
| 4,848,360 A * | 7/1989 | Palsgard ............. A61F 5/56 600/586 |
| 4,851,816 A | 7/1989 | Macias et al. |
| 4,858,611 A | 8/1989 | Elliott |
| 4,860,759 A | 8/1989 | Kahn et al. |
| 4,862,144 A | 8/1989 | Tao |
| 4,869,266 A | 9/1989 | Taylor et al. |
| 4,884,578 A | 12/1989 | Morgenstern |
| 4,889,123 A | 12/1989 | Lee |
| 4,889,130 A | 12/1989 | Lee |
| 4,890,344 A | 1/1990 | Walker |
| 4,893,633 A | 1/1990 | Lee |
| 4,895,155 A | 1/1990 | Lee |
| 4,897,890 A | 2/1990 | Walker |
| 4,908,895 A | 3/1990 | Walker |
| 4,926,866 A | 5/1990 | Lee |
| 4,991,244 A | 2/1991 | Walker |
| 5,062,169 A | 11/1991 | Kennedy et al. |
| 5,079,535 A | 1/1992 | Neuman et al. |
| 5,113,869 A | 5/1992 | Nappholz et al. |
| 5,144,706 A | 9/1992 | Walker et al. |
| 5,170,522 A | 12/1992 | Walker |
| 5,178,151 A | 1/1993 | Sackner |
| 5,197,490 A | 3/1993 | Steiner et al. |
| 5,206,807 A | 4/1993 | Hatke et al. |
| 5,226,416 A | 7/1993 | Bethune et al. |
| 5,291,013 A * | 3/1994 | Nafarrate ............. A61B 5/113 128/925 |
| 5,435,315 A | 7/1995 | McPhee et al. |
| 5,445,159 A | 8/1995 | Cheng |
| 5,454,376 A | 10/1995 | Stephens |
| 5,459,452 A | 10/1995 | DePonte |
| 5,485,848 A | 1/1996 | Jackson et al. |
| 5,505,199 A | 4/1996 | Kim |
| 5,509,154 A | 4/1996 | Shafer et al. |
| 5,515,865 A | 5/1996 | Scanlon |
| 5,564,140 A | 10/1996 | Shoenhair et al. |
| 5,610,987 A * | 3/1997 | Harley ................ A61B 7/04 381/114 |
| 5,642,546 A | 7/1997 | Shoenhair |
| 5,652,484 A | 7/1997 | Shafer et al. |
| 5,675,855 A | 10/1997 | Culp |
| 5,684,460 A * | 11/1997 | Scanlon ............. A61B 5/6892 340/573.1 |
| 5,699,038 A | 12/1997 | Ulrich et al. |
| 5,724,990 A | 3/1998 | Ogino |
| 5,765,246 A | 6/1998 | Shoenhair |
| 5,771,511 A | 6/1998 | Kummer et al. |
| 5,796,340 A | 8/1998 | Miller |
| 5,825,293 A | 10/1998 | Ahmed et al. |
| 5,844,488 A | 12/1998 | Musick |
| 5,848,450 A | 12/1998 | Oexman et al. |
| 5,853,005 A | 12/1998 | Scanlon |
| 5,903,941 A | 5/1999 | Shafer et al. |
| 5,904,172 A | 5/1999 | Gifft et al. |
| 5,914,660 A | 6/1999 | Mesibov et al. |
| 5,948,303 A | 9/1999 | Larson |
| 5,964,720 A | 10/1999 | Pelz |
| 5,989,193 A | 11/1999 | Sullivan |
| 6,004,274 A | 12/1999 | Nolan et al. |
| 6,011,477 A * | 1/2000 | Teodorescu ........... A61B 5/113 340/573.1 |
| 6,015,388 A | 1/2000 | Sackner et al. |
| 6,024,699 A | 2/2000 | Surwit et al. |
| 6,036,660 A | 3/2000 | Toms |
| 6,037,723 A | 3/2000 | Shafer et al. |
| 6,047,201 A | 4/2000 | Jackson, III |
| 6,058,537 A | 5/2000 | Larson |
| 6,062,216 A | 5/2000 | Corn |
| 6,108,844 A | 8/2000 | Kraft et al. |
| 6,120,441 A | 9/2000 | Griebel |
| 6,146,332 A | 11/2000 | Pinsonneault et al. |
| 6,147,592 A | 11/2000 | Ulrich et al. |
| 6,155,976 A | 12/2000 | Sackner et al. |
| 6,159,147 A | 12/2000 | Lichter et al. |
| 6,161,231 A | 12/2000 | Kraft et al. |
| 6,202,239 B1 | 3/2001 | Ward et al. |
| 6,208,250 B1 | 3/2001 | Dixon et al. |
| 6,208,897 B1 | 3/2001 | Jorgenson et al. |
| 6,234,642 B1 | 5/2001 | Bokaemper |
| 6,272,378 B1 | 8/2001 | Baumgart-Schmitt |
| 6,352,517 B1 | 3/2002 | Flock et al. |
| 6,357,438 B1 | 3/2002 | Hansen |
| 6,375,621 B1 | 4/2002 | Sullivan |
| 6,386,201 B1 | 5/2002 | Fard |
| 6,396,224 B1 | 5/2002 | Luff et al. |
| 6,397,419 B1 | 6/2002 | Mechache |
| 6,438,776 B2 | 8/2002 | Ferrand et al. |
| 6,450,957 B1 | 9/2002 | Yoshimi et al. |
| 6,468,234 B1 * | 10/2002 | Van der Loos .......... A61B 5/01 128/920 |
| 6,483,264 B1 | 11/2002 | Shafer et al. |
| 6,485,441 B2 | 11/2002 | Woodward |
| 6,491,647 B1 | 12/2002 | Bridger et al. |
| 6,492,634 B2 | 12/2002 | Marchitto et al. |
| 6,546,580 B2 | 4/2003 | Shimada |
| 6,547,743 B2 | 4/2003 | Brydon |
| 6,553,242 B1 | 4/2003 | Sarussi |
| 6,553,256 B1 | 4/2003 | Jorgenson et al. |
| 6,561,047 B1 | 5/2003 | Gladney |
| 6,566,833 B2 | 5/2003 | Bartlett |
| 6,656,116 B2 | 12/2003 | Kim et al. |
| 6,686,711 B2 | 2/2004 | Rose et al. |

(56) References Cited

U.S. PATENT DOCUMENTS

| | | |
|---|---|---|
| 6,708,357 B2 | 3/2004 | Gaboury et al. |
| 6,719,708 B1 | 4/2004 | Jansen |
| 6,748,814 B2 | 6/2004 | Ishida et al. |
| 6,763,541 B2 | 7/2004 | Mahoney et al. |
| 6,778,090 B2 | 8/2004 | Newham |
| 6,804,848 B1 | 10/2004 | Rose |
| 6,832,397 B2 | 12/2004 | Gaboury et al. |
| 6,840,117 B2 | 1/2005 | Hubbard, Jr. |
| 6,840,907 B1 | 1/2005 | Brydon |
| 6,847,301 B1 | 1/2005 | Olson |
| 6,858,006 B2 | 2/2005 | MacCarter et al. |
| 6,878,121 B2 | 4/2005 | Krausman |
| 6,883,191 B2 | 4/2005 | Gaboury et al. |
| 6,897,773 B2 | 5/2005 | Ridley |
| 6,910,238 B2 | 6/2005 | Biggie et al. |
| 6,970,742 B2 | 11/2005 | Mann et al. |
| 6,976,967 B2 | 12/2005 | Dahl et al. |
| 6,984,207 B1 * | 1/2006 | Sullivan ............... A61B 5/0002 600/300 |
| 6,993,378 B2 | 1/2006 | Wiederhold et al. |
| 6,993,380 B1 | 1/2006 | Modarres |
| 7,035,432 B2 | 4/2006 | Szuba |
| 7,041,049 B1 | 5/2006 | Raniere |
| 7,077,810 B2 | 7/2006 | Lange et al. |
| 7,150,718 B2 | 12/2006 | Okada |
| 7,219,561 B2 | 5/2007 | Okada |
| 7,237,287 B2 | 7/2007 | Weismiller et al. |
| 7,246,619 B2 | 7/2007 | Truschel et al. |
| 7,253,366 B2 | 8/2007 | Bhai |
| 7,304,580 B2 | 12/2007 | Sullivan et al. |
| 7,314,451 B2 | 1/2008 | Halperin et al. |
| 7,321,811 B1 | 1/2008 | Rawls-Meehan |
| 7,330,127 B2 | 2/2008 | Price et al. |
| 7,387,124 B2 | 6/2008 | Noda et al. |
| 7,389,554 B1 | 6/2008 | Rose |
| 7,396,331 B2 | 7/2008 | Mack |
| 7,429,247 B2 | 9/2008 | Okada et al. |
| 7,437,787 B2 | 10/2008 | Bhai |
| 7,465,280 B2 | 12/2008 | Rawls-Meehan |
| 7,480,951 B2 | 1/2009 | Weismiller |
| 7,506,390 B2 | 3/2009 | Dixon et al. |
| 7,513,003 B2 | 4/2009 | Mossbeck |
| 7,520,006 B2 | 4/2009 | Menkedick et al. |
| 7,522,062 B2 | 4/2009 | Mossbeck |
| 7,524,279 B2 | 4/2009 | Auphan |
| 7,532,934 B2 | 5/2009 | Lee et al. |
| 7,538,659 B2 | 5/2009 | Ulrich |
| 7,568,246 B2 | 8/2009 | Weismiller et al. |
| 7,637,859 B2 | 12/2009 | Lindback et al. |
| 7,652,581 B2 | 1/2010 | Gentry et al. |
| 7,654,948 B2 | 2/2010 | Kaplan et al. |
| 7,666,151 B2 | 2/2010 | Sullivan et al. |
| 7,669,263 B2 | 3/2010 | Menkedick et al. |
| 7,676,872 B2 | 3/2010 | Block et al. |
| 7,685,663 B2 | 3/2010 | Rawls-Meehan |
| 7,699,784 B2 | 4/2010 | Wan et al. |
| 7,717,848 B2 | 5/2010 | Heruth et al. |
| 7,749,154 B2 | 7/2010 | Cornel |
| 7,784,128 B2 | 8/2010 | Kramer |
| 7,785,257 B2 | 8/2010 | Mack et al. |
| 7,805,785 B2 | 10/2010 | Rawls-Meehan |
| 7,835,529 B2 | 11/2010 | Hernandez et al. |
| 7,841,031 B2 | 11/2010 | Rawls-Meehan |
| 7,849,545 B2 | 12/2010 | Flocard et al. |
| 7,854,031 B2 | 12/2010 | Rawls-Meehan |
| 7,860,723 B2 | 12/2010 | Rawls-Meehan |
| 7,862,523 B2 | 1/2011 | Ruotoistenmaki |
| 7,865,988 B2 | 1/2011 | Koughan et al. |
| 7,866,212 B2 | 1/2011 | Ariav et al. |
| 7,868,757 B2 | 1/2011 | Radivojevic et al. |
| 7,869,903 B2 | 1/2011 | Turner et al. |
| 7,930,783 B2 | 4/2011 | Rawls-Meehan |
| 7,933,669 B2 | 4/2011 | Rawls-Meehan |
| 7,953,613 B2 | 5/2011 | Gizewski |
| 7,954,189 B2 | 6/2011 | Rawls-Meehan |
| 7,956,755 B2 | 6/2011 | Lee et al. |
| 7,967,739 B2 | 6/2011 | Auphan |
| 7,979,169 B2 | 7/2011 | Rawls-Meehan |
| 8,002,553 B2 | 8/2011 | Hastlestad et al. |
| 8,019,486 B2 | 9/2011 | Rawls-Meehan |
| 8,020,230 B2 | 9/2011 | Rawls-Meehan |
| 8,028,363 B2 | 10/2011 | Rawls-Meehan |
| 8,032,263 B2 | 10/2011 | Rawls-Meehan |
| 8,032,960 B2 | 10/2011 | Rawls-Meehan |
| 8,046,114 B2 | 10/2011 | Rawls-Meehan |
| 8,046,115 B2 | 10/2011 | Rawls-Meehan |
| 8,046,116 B2 | 10/2011 | Rawls-Meehan |
| 8,046,117 B2 | 10/2011 | Rawls-Meehan |
| 8,050,805 B2 | 11/2011 | Rawls-Meehan |
| 8,052,612 B2 | 11/2011 | Tang |
| 8,065,764 B2 | 11/2011 | Kramer |
| 8,069,852 B2 | 12/2011 | Burton |
| 8,073,535 B2 | 12/2011 | Jung et al. |
| 8,078,269 B2 | 12/2011 | Suzuki et al. |
| 8,078,336 B2 | 12/2011 | Rawls-Meehan |
| 8,078,337 B2 | 12/2011 | Rawls-Meehan |
| 8,083,682 B2 | 12/2011 | Dalal et al. |
| 8,090,478 B2 | 1/2012 | Skinner et al. |
| 8,092,399 B2 | 1/2012 | Sasaki |
| 8,094,013 B1 | 1/2012 | Lee |
| 8,096,960 B2 | 1/2012 | Loree et al. |
| 8,146,191 B2 | 4/2012 | Bobey et al. |
| 8,150,562 B2 | 4/2012 | Rawls-Meehan |
| 8,166,589 B2 | 5/2012 | Hijlkema |
| 8,177,724 B2 | 5/2012 | Derchak et al. |
| 8,181,296 B2 | 5/2012 | Rawls-Meehan |
| 8,266,742 B2 | 9/2012 | Andrienko |
| 8,272,892 B2 | 9/2012 | McNeely et al. |
| 8,276,585 B2 | 10/2012 | Buckley |
| 8,279,057 B2 | 10/2012 | Hirose |
| 8,280,748 B2 | 10/2012 | Allen |
| 8,281,433 B2 | 10/2012 | Riley et al. |
| 8,282,452 B2 | 10/2012 | Grigsby et al. |
| 8,284,047 B2 | 10/2012 | Collins, Jr. |
| 8,287,452 B2 | 10/2012 | Young et al. |
| 8,336,369 B2 | 12/2012 | Mahoney |
| 8,341,784 B2 | 1/2013 | Scott |
| 8,341,786 B2 | 1/2013 | Oexman et al. |
| 8,348,840 B2 | 1/2013 | Heit et al. |
| 8,350,709 B2 | 1/2013 | Receveur |
| 8,375,488 B2 | 2/2013 | Rawls-Meehan |
| 8,376,954 B2 | 2/2013 | Lange et al. |
| 8,382,484 B2 | 2/2013 | Wetmore et al. |
| 8,386,008 B2 | 2/2013 | Yuen et al. |
| 8,398,538 B2 | 3/2013 | Dothie |
| 8,403,865 B2 | 3/2013 | Halperin et al. |
| 8,413,274 B2 | 4/2013 | Weismiller et al. |
| 8,421,606 B2 | 4/2013 | Collins, Jr. et al. |
| 8,428,696 B2 | 4/2013 | Foo |
| 8,444,558 B2 | 5/2013 | Young et al. |
| 8,491,492 B2 | 7/2013 | Shinar et al. |
| 8,517,953 B2 | 8/2013 | Lange et al. |
| 8,620,615 B2 | 12/2013 | Oexman |
| 8,672,853 B2 | 3/2014 | Young |
| 8,679,034 B2 | 3/2014 | Halperin et al. |
| 8,769,747 B2 | 7/2014 | Mahoney et al. |
| 8,840,564 B2 | 9/2014 | Pinhas et al. |
| 8,931,329 B2 | 1/2015 | Mahoney et al. |
| 8,966,689 B2 | 3/2015 | McGuire et al. |
| 8,973,183 B1 | 3/2015 | Palashewski et al. |
| 8,984,687 B2 | 3/2015 | Stusynski et al. |
| 9,131,902 B2 | 9/2015 | Halperin et al. |
| 9,265,445 B2 | 2/2016 | Shinar et al. |
| 9,396,646 B2 | 7/2016 | Bischoff et al. |
| 2002/0013717 A1 | 1/2002 | Ando et al. |
| 2002/0030154 A1 | 3/2002 | Marchitto et al. |
| 2002/0070866 A1 | 6/2002 | Newham |
| 2002/0082867 A1 | 6/2002 | MacCarter et al. |
| 2002/0124311 A1 | 9/2002 | Peftoulidis |
| 2002/0133067 A1 | 9/2002 | Jackson |
| 2002/0161290 A1 | 10/2002 | Chance |
| 2002/0196148 A1 | 12/2002 | Nunome |
| 2003/0045806 A1 | 3/2003 | Brydon |
| 2003/0066529 A1 | 4/2003 | Truschel et al. |

(56) References Cited

U.S. PATENT DOCUMENTS

| | | |
|---|---|---|
| 2003/0069510 A1 | 4/2003 | Semler |
| 2003/0078505 A1 | 4/2003 | Kim et al. |
| 2003/0128125 A1 | 6/2003 | Burbank et al. |
| 2003/0130568 A1 | 7/2003 | Vodyanoy et al. |
| 2003/0135097 A1 | 7/2003 | Wiederhold et al. |
| 2003/0158494 A1 | 8/2003 | Dahl et al. |
| 2003/0164762 A1 | 9/2003 | Ridley |
| 2003/0166995 A1 | 9/2003 | Jansen |
| 2003/0182728 A1 | 10/2003 | Chapman et al. |
| 2003/0221261 A1 | 12/2003 | Tarbet et al. |
| 2004/0034289 A1 | 2/2004 | Teller et al. |
| 2004/0044290 A1 | 3/2004 | Ward et al. |
| 2004/0049132 A1 | 3/2004 | Barron et al. |
| 2004/0111045 A1 | 6/2004 | Sullivan et al. |
| 2004/0116784 A1 | 6/2004 | Gavish |
| 2004/0144383 A1 | 7/2004 | Thomas et al. |
| 2004/0147969 A1 | 7/2004 | Mann et al. |
| 2004/0167418 A1 | 8/2004 | Nguyen et al. |
| 2004/0167580 A1 | 8/2004 | Mann et al. |
| 2004/0194220 A1 | 10/2004 | Price et al. |
| 2004/0215049 A1 | 10/2004 | Zdeblick et al. |
| 2004/0245036 A1 | 12/2004 | Fujita et al. |
| 2004/0249297 A1 | 12/2004 | Pfeiffer et al. |
| 2004/0249314 A1 | 12/2004 | Salla et al. |
| 2005/0010125 A1 | 1/2005 | Joy et al. |
| 2005/0017864 A1 | 1/2005 | Tsoukalis |
| 2005/0022606 A1* | 2/2005 | Partin ............ A61B 5/0816 73/773 |
| 2005/0027416 A1* | 2/2005 | Basir ............ A61B 5/6887 701/36 |
| 2005/0038326 A1 | 2/2005 | Mathur |
| 2005/0043652 A1 | 2/2005 | Lovett et al. |
| 2005/0053262 A1 | 3/2005 | Szuba |
| 2005/0065571 A1 | 3/2005 | Imran |
| 2005/0113673 A1 | 3/2005 | Avinash et al. |
| 2005/0075542 A1 | 4/2005 | Goldreich |
| 2005/0113703 A1 | 5/2005 | Farringdon et al. |
| 2005/0115561 A1 | 6/2005 | Stahmann et al. |
| 2005/0154422 A1 | 7/2005 | Band et al. |
| 2005/0177051 A1 | 8/2005 | Almen |
| 2005/0190068 A1 | 9/2005 | Gentry et al. |
| 2005/0283039 A1 | 12/2005 | Cornel |
| 2006/0020178 A1 | 1/2006 | Sotos et al. |
| 2006/0020221 A1 | 1/2006 | Silpachai et al. |
| 2006/0024151 A1 | 2/2006 | Keith et al. |
| 2006/0031996 A1 | 2/2006 | Rawls-Meehan |
| 2006/0047217 A1 | 3/2006 | Mirtalebi |
| 2006/0050930 A1 | 3/2006 | Dearborn |
| 2006/0063982 A1* | 3/2006 | Sullivan ............ A61B 5/113 600/301 |
| 2006/0152378 A1 | 7/2006 | Lokhorst |
| 2006/0162074 A1 | 7/2006 | Bader |
| 2006/0224326 A1 | 10/2006 | Ores et al. |
| 2006/0271400 A1 | 11/2006 | Clements et al. |
| 2007/0118054 A1 | 5/2007 | Pinhas et al. |
| 2007/0149883 A1 | 6/2007 | Yesha |
| 2007/0179334 A1 | 8/2007 | Groves et al. |
| 2007/0180047 A1 | 8/2007 | Dong et al. |
| 2007/0180618 A1 | 8/2007 | Weismiller et al. |
| 2007/0276202 A1 | 11/2007 | Raisanen et al. |
| 2007/0276270 A1* | 11/2007 | Tran ............ A61B 5/002 600/508 |
| 2007/0293781 A1* | 12/2007 | Sims ............ G16H 50/30 600/534 |
| 2008/0052837 A1 | 3/2008 | Blumberg |
| 2008/0071200 A1 | 3/2008 | Rawls-Meehan |
| 2008/0077020 A1 | 3/2008 | Young et al. |
| 2008/0092291 A1 | 4/2008 | Rawls-Meehan |
| 2008/0092292 A1 | 4/2008 | Rawls-Meehan |
| 2008/0092293 A1 | 4/2008 | Rawls-Meehan |
| 2008/0092294 A1 | 4/2008 | Rawls-Meehan |
| 2008/0093784 A1 | 4/2008 | Rawls-Meehan |
| 2008/0097774 A1 | 4/2008 | Rawls-Meehan |
| 2008/0097778 A1 | 4/2008 | Rawls-Meehan |
| 2008/0097779 A1 | 4/2008 | Rawls-Meehan |
| 2008/0104750 A1 | 5/2008 | Rawls-Meehan |
| 2008/0104754 A1 | 5/2008 | Rawls-Meehan |
| 2008/0104755 A1 | 5/2008 | Rawls-Meehan |
| 2008/0104756 A1 | 5/2008 | Rawls-Meehan |
| 2008/0104757 A1 | 5/2008 | Rawls-Meehan |
| 2008/0104758 A1 | 5/2008 | Rawls-Meehan |
| 2008/0104759 A1 | 5/2008 | Rawls-Meehan |
| 2008/0104760 A1 | 5/2008 | Rawls-Meehan |
| 2008/0104761 A1 | 5/2008 | Rawls-Meehan |
| 2008/0109959 A1 | 5/2008 | Rawls-Meehan |
| 2008/0109964 A1 | 5/2008 | Flocard et al. |
| 2008/0109965 A1 | 5/2008 | Mossbeck |
| 2008/0115272 A1 | 5/2008 | Rawls-Meehan |
| 2008/0115273 A1 | 5/2008 | Rawls-Meehan |
| 2008/0115274 A1 | 5/2008 | Rawls-Meehan |
| 2008/0115275 A1 | 5/2008 | Rawls-Meehan |
| 2008/0115276 A1 | 5/2008 | Rawls-Meehan |
| 2008/0115277 A1 | 5/2008 | Rawls-Meehan |
| 2008/0115278 A1 | 5/2008 | Rawls-Meehan |
| 2008/0115279 A1 | 5/2008 | Rawls-Meehan |
| 2008/0115280 A1 | 5/2008 | Rawls-Meehan |
| 2008/0115281 A1 | 5/2008 | Rawls-Meehan |
| 2008/0115282 A1 | 5/2008 | Rawls-Meehan |
| 2008/0120775 A1 | 5/2008 | Rawls-Meehan |
| 2008/0120776 A1 | 5/2008 | Rawls-Meehan |
| 2008/0120777 A1 | 5/2008 | Rawls-Meehan |
| 2008/0120778 A1 | 5/2008 | Rawls-Meehan |
| 2008/0120779 A1 | 5/2008 | Rawls-Meehan |
| 2008/0120784 A1 | 5/2008 | Warner et al. |
| 2008/0122616 A1 | 5/2008 | Warner |
| 2008/0126122 A1 | 5/2008 | Warner et al. |
| 2008/0126132 A1 | 5/2008 | Warner |
| 2008/0127418 A1 | 6/2008 | Rawls-Meehan |
| 2008/0147442 A1 | 6/2008 | Warner |
| 2008/0127424 A1 | 7/2008 | Rawls-Meehan |
| 2008/0162171 A1 | 7/2008 | Rawls-Meehan |
| 2008/0189865 A1 | 8/2008 | Bhai |
| 2008/0275314 A1 | 11/2008 | Mack et al. |
| 2008/0281611 A1 | 11/2008 | Rawls-Meehan |
| 2008/0281612 A1 | 11/2008 | Rawls-Meehan |
| 2008/0281613 A1 | 11/2008 | Rawls-Meehan |
| 2008/0288272 A1 | 11/2008 | Rawls-Meehan |
| 2008/0288273 A1 | 11/2008 | Rawls-Meehan |
| 2008/0306351 A1 | 12/2008 | Izumi |
| 2008/0307582 A1 | 12/2008 | Flocard et al. |
| 2009/0018853 A1 | 1/2009 | Rawls-Meehan |
| 2009/0018854 A1 | 1/2009 | Rawls-Meehan |
| 2009/0018855 A1 | 1/2009 | Rawls-Meehan |
| 2009/0018856 A1 | 1/2009 | Rawls-Meehan |
| 2009/0018857 A1 | 1/2009 | Rawls-Meehan |
| 2009/0018858 A1 | 1/2009 | Rawls-Meehan |
| 2009/0024406 A1 | 1/2009 | Rawls-Meehan |
| 2009/0037205 A1 | 2/2009 | Rawls-Meehan |
| 2009/0043595 A1 | 2/2009 | Rawls-Meehan |
| 2009/0064420 A1 | 3/2009 | Rawls-Meehan |
| 2009/0100599 A1 | 4/2009 | Rawls-Meehan |
| 2009/0112713 A1 | 4/2009 | Jung et al. |
| 2009/0121660 A1 | 5/2009 | Rawls-Meehan |
| 2009/0139029 A1 | 6/2009 | Rawls-Meehan |
| 2009/0203972 A1 | 8/2009 | Henehgan et al. |
| 2009/0275808 A1 | 11/2009 | DiMaio et al. |
| 2009/0314354 A1 | 12/2009 | Chaffee |
| 2010/0025900 A1 | 2/2010 | Rawls-Meehan |
| 2010/0090383 A1 | 4/2010 | Rawls-Meehan |
| 2010/0094139 A1 | 4/2010 | Brauers et al. |
| 2010/0099954 A1 | 4/2010 | Dickinson et al. |
| 2010/0152546 A1 | 6/2010 | Behan et al. |
| 2010/0170043 A1 | 7/2010 | Young et al. |
| 2010/0174198 A1 | 7/2010 | Young et al. |
| 2010/0174199 A1 | 7/2010 | Young et al. |
| 2010/0191136 A1 | 7/2010 | Wolford |
| 2010/0199432 A1 | 8/2010 | Rawls-Meehan |
| 2010/0231421 A1 | 9/2010 | Rawls-Meehan |
| 2010/0302044 A1 | 12/2010 | Chacon et al. |
| 2010/0317930 A1 | 12/2010 | Oexman et al. |
| 2011/0001622 A1 | 1/2011 | Gentry |
| 2011/0010014 A1 | 1/2011 | Oexman et al. |
| 2011/0015495 A1 | 1/2011 | Dothie et al. |

(56) References Cited

U.S. PATENT DOCUMENTS

| | | |
|---|---|---|
| 2011/0041592 A1 | 2/2011 | Schmoeller et al. |
| 2011/0068935 A1 | 3/2011 | Riley et al. |
| 2011/0087113 A1 | 4/2011 | Mack et al. |
| 2011/0094041 A1 | 4/2011 | Rawls-Meehan |
| 2011/0115635 A1 | 5/2011 | Petrovski et al. |
| 2011/0144455 A1 | 6/2011 | Young et al. |
| 2011/0156915 A1 | 6/2011 | Brauers et al. |
| 2011/0224510 A1 | 9/2011 | Oakhill |
| 2011/0239374 A1 | 10/2011 | Rawls-Meehan |
| 2011/0252569 A1 | 10/2011 | Rawls-Meehan |
| 2011/0258784 A1 | 10/2011 | Rawls-Meehan |
| 2011/0282216 A1 | 11/2011 | Shinar et al. |
| 2011/0283462 A1 | 11/2011 | Rawls-Meehan |
| 2011/0291795 A1 | 12/2011 | Rawls-Meehan |
| 2011/0291842 A1 | 12/2011 | Oexman |
| 2011/0295083 A1 | 12/2011 | Doelling et al. |
| 2011/0302720 A1 | 12/2011 | Yakam et al. |
| 2011/0306844 A1 | 12/2011 | Young |
| 2012/0025992 A1 | 2/2012 | Tallent et al. |
| 2012/0053423 A1 | 3/2012 | Kenalty et al. |
| 2012/0053424 A1 | 3/2012 | Kenalty et al. |
| 2012/0056729 A1 | 3/2012 | Rawls-Meehan |
| 2012/0057685 A1 | 3/2012 | Rawls-Meehan |
| 2012/0090698 A1 | 4/2012 | Giori et al. |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0138067 A1 | 6/2012 | Rawls-Meehan |
| 2012/0154155 A1 | 6/2012 | Brasch |
| 2012/0186019 A1 | 7/2012 | Rawls-Meehan |
| 2012/0198632 A1 | 8/2012 | Rawls-Meehan |
| 2012/0311790 A1 | 12/2012 | Nomura et al. |
| 2013/0160212 A1 | 6/2013 | Oexman et al. |
| 2013/0174347 A1 | 7/2013 | Oexman et al. |
| 2013/0227787 A1 | 9/2013 | Herbst et al. |
| 2014/0007656 A1 | 1/2014 | Mahoney |
| 2014/0137332 A1 | 5/2014 | McGuire et al. |
| 2014/0182061 A1 | 7/2014 | Zaiss |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski |
| 2014/0259431 A1 | 9/2014 | Fleury |
| 2014/0259433 A1 | 9/2014 | Nunn et al. |
| 2014/0259434 A1 | 9/2014 | Nunn et al. |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2014/0313700 A1 | 10/2014 | Connell et al. |
| 2015/0007393 A1 | 1/2015 | Palashewski et al. |
| 2015/0008710 A1 | 1/2015 | Young et al. |
| 2015/0025327 A1 | 1/2015 | Young et al. |
| 2015/0026896 A1 | 1/2015 | Fleury et al. |
| 2015/0136146 A1 | 5/2015 | Hood et al. |
| 2015/0157137 A1 | 6/2015 | Nunn et al. |
| 2015/0157519 A1 | 6/2015 | Stusynski et al. |
| 2015/0182033 A1 | 7/2015 | Brosnan et al. |
| 2015/0182397 A1 | 7/2015 | Palashewski et al. |
| 2015/0182399 A1 | 7/2015 | Palashewski et al. |
| 2015/0182418 A1 | 7/2015 | Zaiss |
| 2015/0290059 A1 | 10/2015 | Brosnan et al. |
| 2015/0374137 A1 | 12/2015 | Mahoney et al. |
| 2016/0100696 A1 | 4/2016 | Palashewski et al. |

FOREIGN PATENT DOCUMENTS

| | | |
|---|---|---|
| JP | 2004-113618 | 4/2004 |
| JP | 2004-130012 | 4/2004 |
| JP | 2004-229875 | 8/2004 |
| JP | 2007-125337 | 5/2007 |
| JP | 2008-259745 | 10/2008 |
| JP | 2010-094379 | 4/2010 |
| WO | WO 2003/082111 | 10/2003 |
| WO | WO 2004/045407 | 6/2004 |
| WO | WO 2004/082549 | 9/2004 |
| WO | WO 2005/000108 | 1/2005 |
| WO | WO 2005/055824 | 6/2005 |
| WO | WO 2005/079530 | 9/2005 |
| WO | WO 2005/120339 | 12/2005 |
| WO | WO 2008/128250 | 10/2008 |
| WO | WO 2009/108228 | 9/2009 |
| WO | WO 2009/123641 | 10/2009 |

* cited by examiner

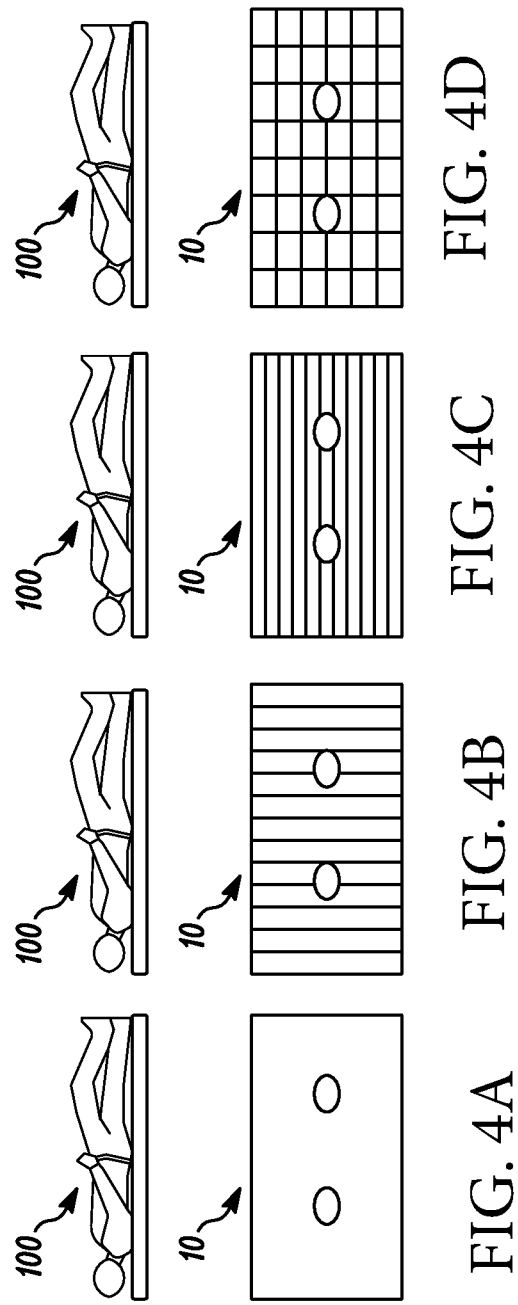

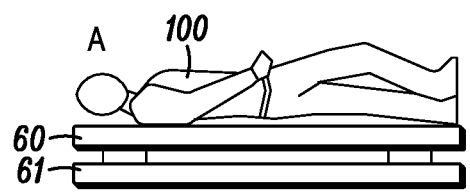
FIG. 12A
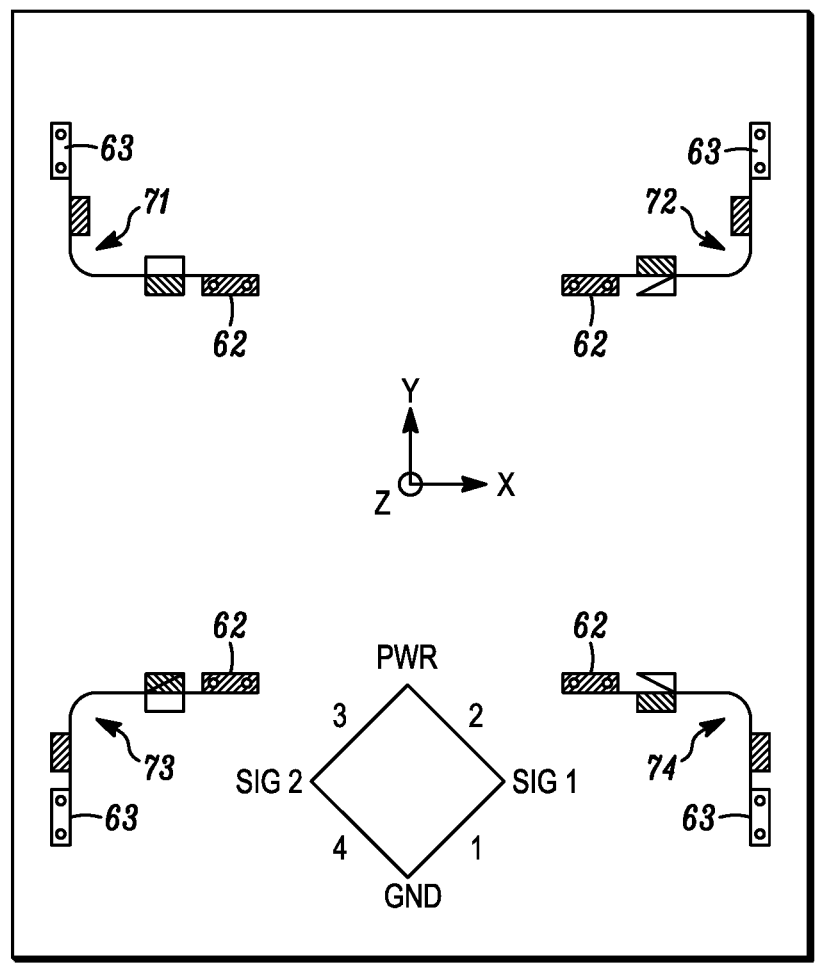
FIG. 12B

METHOD AND APPARATUS FOR MONITORING VITAL SIGNS REMOTELY

CROSS-REFERENCE TO RELATED APPLICATIONS

The present application is a continuation of U.S. Ser. No. 15/349,406, filed Nov. 11, 2016, which is a divisional of and claims priority to U.S. application Ser. No. 11/849,051, filed on Aug. 31, 2007, which claims the benefit of priority to U.S. Provisional Application No. 60/846,642, filed Sep. 22, 2006, all of which are hereby incorporated in their entirety by reference.

TECHNICAL FIELD

The present method and apparatus relate to monitoring vital signs, such as the presence of a heartbeat and breathing, in an human or animal.

BACKGROUND

There are a variety of settings in which monitoring one or more vital signs of an individual can be important. For example, sleeping infants may be monitored for respiration or heartbeat, to alert parents or guardians to changes in the infant's heart of breathing status, caused for example, by sudden infant death syndrome (SIDS) or accidental suffocation. In a hospital setting, such as an emergency room (ER) waiting area, ambulance, or where an individual has been hospitalized with a cardiac condition, it may be important to monitor the individual's heart rate, both to provide an alert for a catastrophic systems failure or to monitor changes in heart rate status, e.g., in response to certain medications. Elder care patients who are at risk for cardiovascular failure or decline may also need vital-signs monitoring, to alert an attendant to dramatic changes in health status or the need for drug intervention. Typically, these are all settings in which an individual is lying or sitting at rest.

A number of devices designed for monitoring vital signs are known. In a hospital setting where a patient's heart rate and function are being monitored, it is usual to record a continuous electrocardiogram (EKG or ECG) of the patient. This is performed by attaching a number of electrodes to various points of the patient's chest and back region, to measure the rhythmic electrical activity of the heart. An EKG hookup tends to be uncomfortable and confining over extended periods, and requires a trained medical professional to apply the electrodes properly and to operate the device. For example, during sleep, the electrodes can come off the patient and cause a false alarm. The cost and inconvenience of EKG monitoring make it impractical for many health-monitoring settings, such as non critical hospital patients, infant or elder care monitoring.

A less intrusive means for measuring heart rate is a mechanical inertial device known as a ballistocardiograph, which is designed to record the volume of blood passing through the heart, at any period in time, based on the body's recoil as blood is ejected from the heart ventricles with each heartbeat. Such devices, as exemplified by U.S. Pat. No. 4,679,569, tend to have a rigid, mechanical plate structure and a complicated mechanism for measuring changes in plate motion.

There exists a need for a monitoring apparatus that has a simplified, relatively inexpensive construction, can be used comfortably by an individual on a mattress or chair, does not require any patient hookup, can be used easily by an untrained person, and provides accurate heart and respiration-rate information to a monitoring site or person.

SUMMARY

The invention includes, in one aspect, an apparatus for monitoring heart and respiration rates of a human subject at rest, comprising, in operative condition, (a) a sensing unit having (i) a fluid or gas-filled pad adapted to be placed on a bed, crib, or chair support, for cushioning at least an upper body portion of a subject lying on or resting against the support, mattress or cushion, and (ii) a pressure sensor in fluid communication with gas or fluid in said unit, for generating electrical signals in response to pressure variations within the gas or fluid in the pad, and (b) a monitoring unit operatively connected to said pressure sensor, for (i) receiving signals therefrom, (ii) generating from said signals, information about the heart and respiration rates of the subject, and (iii) relaying such information to a monitoring station or individual.

In some embodiments, the pad is a fluid-filled pad. In some embodiments, the pad is a gas-filled pad.

In some embodiments, the apparatus further includes a pressure-control unit comprising a pump in fluid or gas communication with the pad and a controller operatively connected to the pump for maintaining fluid or gas within the pad at a selected pressure or within a defined pressure range.

In some embodiments, the pad comprises a single fluid or gas-filled chamber, having a pressure sensor in fluid or gas communication therewith, for generating electrical signals in response to pressure changes within the chamber.

In other embodiments, the pad includes at least two independent, fluid or gas-filled chambers, each of which has a pressure sensor in fluid communication therewith, for generating electrical signals in response to pressure changes within the associated chamber.

In some embodiments, the apparatus further includes an ambient-null device comprising a fluid or gas-filled ambient pad, a weight carried on the ambient pad, for exerting pressure thereon, and an ambient pressure sensor in fluid or gas communication with fluid in the ambient pad, for generating electrical signals in response to pressure changes within the fluid or gas, in response to ambient motion in the vicinity of the subject, wherein said monitoring unit is operatively connected to said ambient pressure sensor, for (i) receiving signals therefrom, and (ii) processing the signals received from the first-mentioned and ambient pressure sensors, to filter such ambient motion from motion related to the subject's heart and respiration rates.

In some embodiments, the monitoring unit includes a processor operative to (i) generate heart-rate information of the subject, based on time-dependent signals having frequency components in the range from about 0.1 to about 10 Hz, and (ii) generate respiration rate information of the subject based on time-dependent signals having frequency components in the range less than about 1 Hz. In particular embodiments, the information generated by the signal processor further includes blood-pressure information.

In some embodiments, the pad includes upper and lower independent, fluid or gas-filled chambers, each of which has a pressure sensor in fluid communication therewith, for generating electrical signals in response to pressure changes within the associated chamber, and the information generated by the processor includes information about the orientation of the individual with respect to the pad, based on a characteristic ventral, dorsal or lateral signals produced by processing the two separate signals generated for the two chambers.

In some embodiments, the monitoring unit includes a remote monitor, and a transmitter for transmitting such heart and respiration rate information from the processor to the monitor.

In some embodiments, the pad further includes temperature sensor for measuring the temperature of the individual on the pad.

In another aspect, a sensor unit for use with a monitoring unit is provided, for monitoring heart and respiration rates of a human subject at rest, comprising, in operative condition, (a) a fluid or gas-filled pad adapted to be placed on a bed, crib, or chair support, for cushioning at least an upper-body portion of a subject lying on or resting against the support, and (b) a pressure sensor in fluid communication with fluid in said unit, for generating electrical signals in response to pressure variations within the fluid or gas, and adapted to be operatively connected to such a monitor.

In some embodiments, the pad includes as single fluid or gas-filled chamber having a pressure sensor in fluid of gas communication therewith, for generating electrical signals in response to pressure changes within the chamber.

In other embodiments, the pad includes at least two independent, fluid-filled chambers, each of which has a pressure sensor in fluid or gas communication therewith, for generating electrical signals in response to pressure changes within the associated chamber. In some embodiments, the pad is a fluid-filled pad. In some embodiments, the pad is a gas-filled pad.

In another aspect, a method for monitoring vital signs is provided, including heart and respiration rates, of a human subject lying on or resting against a bed, crib, or chair support, comprising (a) placing between the subject and the support, a fluid or gas-filled pad positioned for cushioning at least an upper-body area of the subject, (b) generating electrical signals in response to pressure variations within the fluid or gas by a pressure sensor in fluid communication with fluid or gas in said pad, and (c) processing the electrical signals received from the pressure sensor to generate information about the heart and respiration rate of the subject.

In another aspect, an apparatus for remotely monitoring heart and respiration rates of a human subject lying on or resting against a bed, crib, or chair support is provided, comprising (a) a pad adapted to the placed between the subject and the support, for cushioning at least an upper body portion of the individual, (b) a sensor on said pad for generating motion-related signals caused by the subject's heartbeat and breathing, (c) a processor operatively connected to said sensor, for (i) receiving time-dependent signals therefrom, and (ii) generating heart-rate information of the subject, based on received time-dependent signals in the range from about 0.1 to about 10 Hz, and respiration rate information of the subject, based on received timed-dependent signals in the range less than about 1 Hz, (d) a remote monitor for use by an individual in monitoring said subject, and (e) a transmitter for transmitting such subject information from the processor to the individual.

In some embodiments, the apparatus further includes an ambient-motion device for generating signals related to ambient motion in the vicinity of the subject, and said processor is operatively connected to said device, for processing the signals received from the device, to filter such ambient motion from motion related to the subject's heart and respiration rates.

In another aspect, an apparatus for monitoring vital signs is provided, including heart and respiration rates, of a human subject lying on or resting against a bed, crib, or chair support, comprising (a) a pad adapted to the placed between the subject and the support, for cushioning at least an upper body portion of the individual, said pad comprising (i) a pair of confronting plates, one adapted to be supported on the mattress, and the other adapted for contact with the chest area of the individual, said plates being spaced apart for relative lateral movement in an XY plane and relative vertical movement in the Z direction, (iii) connecting the two plates, an L-shaped connector attached at opposite ends to the opposing plates and having a pair of laterally extending, orthogonally disposed arms, a strain gauge carried on each arm, in an XY plane, and a strain gauge carried on one of the arms, in a vertical plane, and (b) a monitoring unit operative to transmit to a remote user, information about the heart rate of the individual, based on signals received from the pad's lateral-movement strain gauge devices, and about the respiration rate of the individual, based on signals received from the pad's vertical-movement strain gauge(s).

The apparatus of claim 20, wherein said two opposing plates are substantially rectangular, and connected by said L-shaped connectors in the region of each of the four corners of the two plates.

In some embodiments, the apparatus further includes a vertical-movement strain gauge connecting the two plates, for generating information about the weight applied by the individual on the pad.

In some embodiments, the monitoring unit includes a processor operative to (i) wherein said monitoring unit includes a signal processor operative to (i) generate heart-rate information of the subject, based on time-dependent signals received from each of the plural lateral-movement strain-gauge devices, and having frequency components in the range from about 0.1-10 Hz, and (ii) generate respiration rate information of the subject based on timed-dependent signals having frequency received from the at least one of the vertical-movement strain gauge(s), and having frequency components in the range less than about 1 Hz.

In some embodiments, the monitoring unit includes a remote monitor, and a transmitter for transmitting such heart rate and respiration rate information from the processor to the monitor.

In some embodiments, the pad further includes temperature sensor for measuring the temperature of the individual on the pad.

In some embodiments, the apparatus further includes a weighted strain gauge adapted for attachment to the bed or crib, independent of said pad, for detecting movement of the bed or crib, independent of movement within the pad, and the monitoring unit is operative to remove such independent movement from pad movement detected by the pad strain gauges.

In a related aspect, an apparatus for determining the presence of a subject is provided, comprising:

(a) a sensing unit having (i) a fluid or gas-filled pad adapted to be placed on a bed, crib, or chair support, for cushioning at least an upper body portion of a subject lying on or resting against the support, mattress or cushion, and (ii) a pressure sensor in fluid communication with fluid in said unit, for generating electrical signals in response to pressure variations within the fluid in the pad, and (b) a monitoring unit operatively connected to said pressure sensor, for (i) receiving signals therefrom, (ii) generating from said signals, information about the presence of the subject and (iii) relaying such information to a monitoring station or individual.

In another related aspect, a sensor unit for use with a monitoring unit, for detecting the presence of a subject is provided, comprising:

(a) a fluid or gas-filled pad adapted to be placed on a bed, crib, or chair support, for cushioning at least an upper-body portion of a subject lying on or resting against the support, and (b) a pressure sensor in fluid communication with fluid in said unit, for generating electrical signals in response to pressure variations within the fluid or gas, and adapted to be operatively connected to such a monitor.

A related method for detecting the presence of a subject on or in a bed, crib, or chair support is provided, comprising:

(a) placing on or in the bed, crib, or chair support a fluid or gas-filled pad positioned for cushioning at least an upper-body area of the subject, (b) generating electrical signals in response to pressure variations within the fluid or gas by a pressure sensor in fluid communication with fluid or gas in said pad, and (c) processing the electrical signals received from the pressure sensor to generate information about the presence of the subject.

In a related aspect, an apparatus for monitoring the presence of a subject lying on or resting against a bed, crib, or chair support is provided, comprising:

(a) a pad adapted to the placed between the subject and the support, for cushioning at least an upper body portion of the individual, said pad comprising (i) a pair of confronting plates, one adapted to be supported on the mattress, and the other adapted for contact with the chest area of the individual, said plates being spaced apart for relative lateral movement in an XY plane and relative vertical movement in the Z direction, (iii) connecting the two plates, an L-shaped connector attached at opposite ends to the opposing plates and having a pair of laterally extending, orthogonally disposed arms, a strain gauge carried on each arm, in an XY plane, and a strain gauge carried on one of the arms, in a vertical plane, and (b) a monitoring unit operative to transmit to a remote user, information about the presence of the subject, based on signals received from the pad's strain gauge devices.

Apparatus for monitoring the presence of a subject, rather than health of a subject, may be connected to the internet and may further include any of the additional features described herein.

These and other aspects and embodiments of the present invention will become better apparent in view of the detailed description in conjunction with the accompanying drawings.

BRIEF DESCRIPTION OF THE DRAWINGS

FIGS. 4A-4D are diagrams illustrating alternative embodiments of the sensor shown in FIG. 3.

FIGS. 12A and 12B illustrate components of a two-plate mechanical sensor having orthogonally disposed strain gauges for monitoring heart and respiratory functions. 12A is a side view showing a human subject. 12B is a top view showing the strain gauges connecting the two plates.

DETAILED DESCRIPTION

I. Introduction

A method and apparatus are provided for monitoring the presence and health status of human and animal subjects/patients. The method and apparatus utilize a pad or plate sensor unit adapted to be placed in a bed, cushion mattress, infant crib, or the like for generating health status data corresponding to the subject's cardiac function and/or respiration (i.e. breathing). The pad or plate sensor may be a fluid or gas-filled device, an electromechanical device, an optical device, or a semi-conducting device, depending on the embodiment.

Data generated from the sensor unit may be combined with additional data (e.g., generated by one or more additional sensors), filtered, and relayed to a microprocessor for recording or analysis. Processed data may be used to trigger one or more events. In some examples, the event is to sound an alarm or alert medical professionals to deteriorating health status of a subject. The health status data that trigger an event, and the events that are triggered, may be preselected by a user depend on the particular application.

The method and apparatus are readily integrated with internet/web-based services, wireless telecommunications, advanced audio and video processing, instant messaging, digital and analog signal processing, medical record databases and patient records, and private and public health agencies, thereby linking a subject's health status to any number of services.

Figure 1:
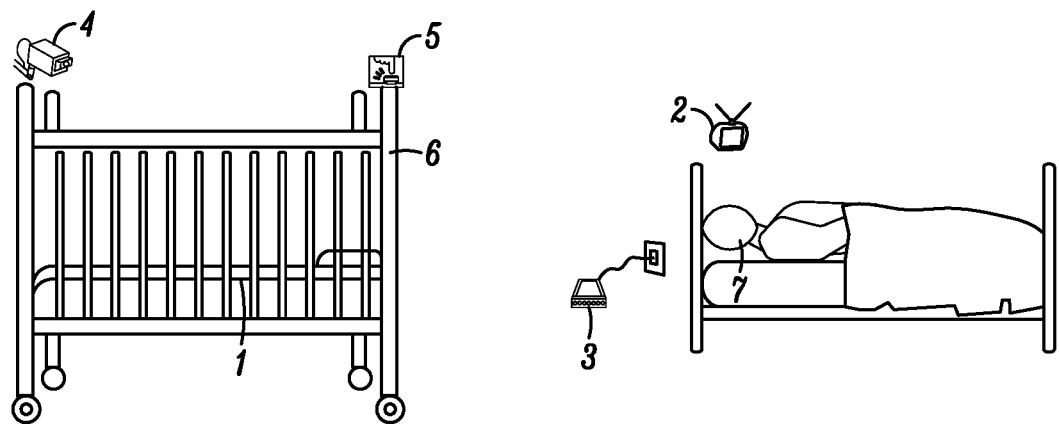
FIG. 1 is a diagram illustrating a system and method for monitoring vital signs in accordance with an embodiment of the invention.
Figure 2:
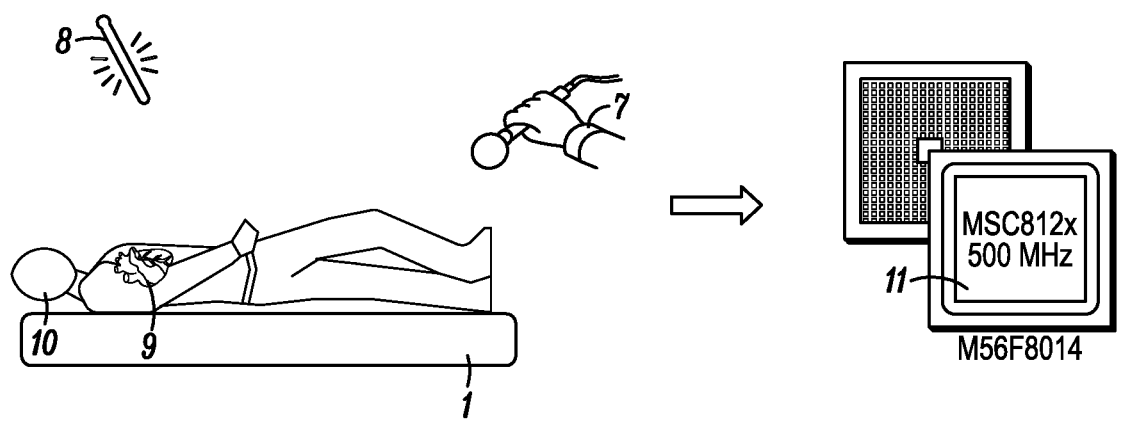
FIG. 2 is a diagram illustrating a system and method for monitoring vital signs in accordance with another embodiment of the invention, illustrating a pad sensing unit that detects heart and respiration from a human subject, optional temperature and audio sensors that provide additional data, and a digital signal processor (DSP) that analyzes data from the mattress pad sensing unit and other data.

FIG. 1 shows an exemplary monitoring method and apparatus. The view illustrates an infant crib 6 with a sensor pad or plate sensor 1 adapted for use as a mattress. A wireless in home monitor 2 is provided, e.g., to allow a parent or guardian 7 to monitor data from the sensor 1 via a wireless phone or internet protocol link 3. The crib is further equipped with a camera 4 to transmit live or delayed video, e.g., to allow the determination of whether the infant, adult, or animal is on its back, front, or sides, by identifying features of the subject, and a panic button 5. A wired or wireless transceiver can also be equipped to communicate between the sensor and the camera, panic button and remote monitor. As shown in FIG. 2, the pad or plate sensor 1 detects heart 9 and respiration vibrations in from the infant subject 10 along with data from optional additional sensors (i.e., a microphone 7 and thermometer 8). These data are transmitted, by wire or wirelessly, to a digital signal processor (DSP) 11, which analyzes the data and triggers appropriate actions.

The method and apparatus are described in more detail, below.

II. Monitoring Apparatus

A feature of the present method and apparatus is a sensor unit adapted for placement on a bed, crib, chair, automotive or avionics seat, or similar rest surface for a human or animal. In some embodiments, the sensor is in the form of a mattress or mattress pad, upon which a subject will rest. In other embodiments, the sensor is in the form of a cushion or cushion pad, upon which a subject will sit or lean. In other embodiments, the sensor is in the form of plate upon which a subject will rest.

Both fluid/gas-filled sensors and electromechanical sensors may be used according to the present method and apparatus. Such sensors may be referred to as ballistocardiographs, monitor-enabled pads or mattress, vital signs sensors, or health status data sensors.

Embodiments of the pad or plate sensor are described, below.

A. Fluid/Gas-Filled Pad Embodiment

Figure 5:
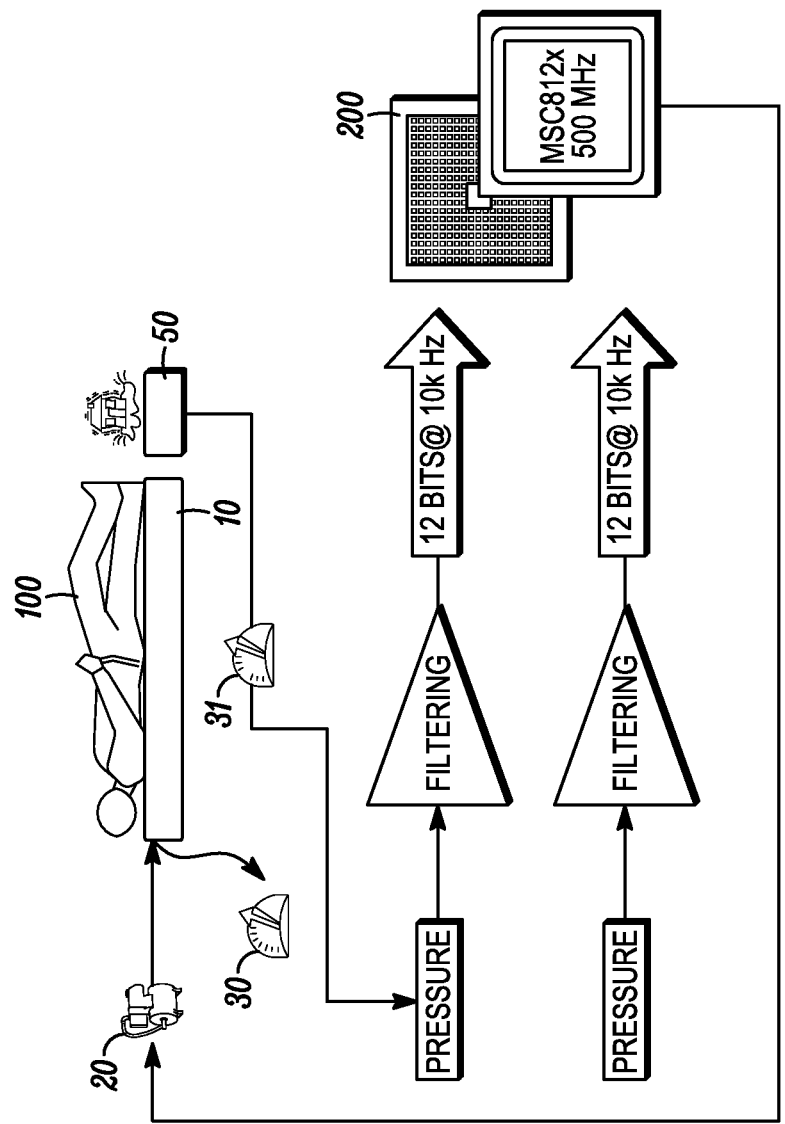
FIG. 5 is a diagram illustrating a system and method for monitoring vital signs in accordance with an alternative embodiment that includes an ambient vibration cancellation device.

In some embodiments, the sensor uses a fluid or gas-filled pad upon which a subject will rest. The fluid/gas-filled pad may be connected to a suitable fluid/gas pump to maintain a desirable pressure and/or volume in the pad. The pad is further connected to an fluid/gas pressure sensor, which monitors the pressure changes in the pad in response to a subject's hear function or respiration. According to this embodiment, incident pressure waves caused by shifting body weight in response to cardiopulmonary activity induces a change in the measured pressure, which data are sampled and processed. This embodiment of the method and apparatus are illustrated in FIGS. 3-5.

Figure 3:
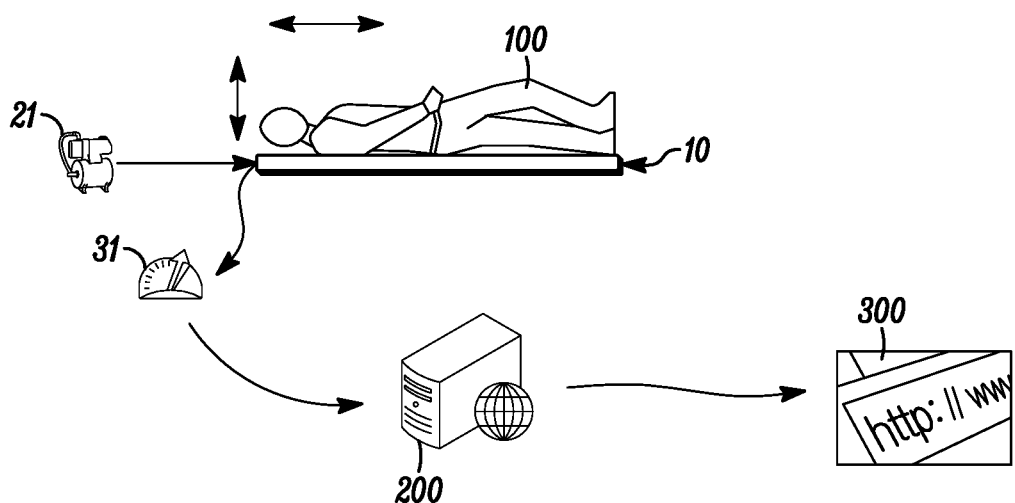
FIG. 3 is a diagram illustrating an embodiment of the system of FIG. 1 that utilizes an air-filled mattress sensor connected to an air pump (i.e., a pressure-control unit) for maintaining pad pressure within a predefined range. Vibrations corresponding to heart and respiration functions are detected by a pressure sensor, communicated to a computer for analysis, and distributed via the internet.

As shown in FIG. 3, the fluid filled pad is a custom air mattress 10 is operably connected to an air pump 21 for filing the pad sensor to a preselected pressure or volume and an air pressure sensor 31 for monitoring the pressure in the mattress 10. Ballistic motion of the subject infant 100 caused by cardiac function and breathing cause pressure variations in the pad sensor 10, which can be detected by the pressure sensor 31, which produces or alters electrical signals in response to pressure variations. A signal (i.e., data; typically electrical) from the pressure sensor 31 is received by a microprocessor 200 for analysis. The raw or processed signal/data may be sent to the internet 300 for distribution.

Figure 3A:
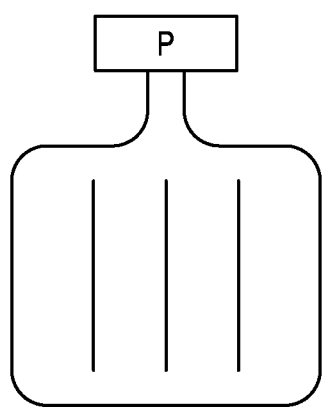
FIGS. 3A and 3B are diagrams illustrating alternative embodiments of the sensor shown in FIG. 3.
Figure 3B:
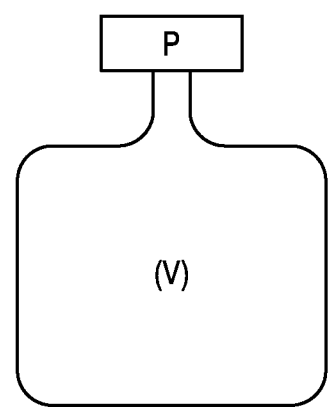

FIGS. 3A and 3B illustrate additional embodiments of custom air mattress 10. In FIG. 3A, air mattress 10 is a bladder or bag containing a fluid (that is, either liquid or gas) with a pressure sensor 31. The incident pressure wave caused by movement of the subject's body induces a change in measured pressure, which is then sampled and used in detector calculations. The design as shown in FIG. 3A can resemble a conventional air mattress, and can include ribbing to provide structural support and to reduce ringing or related interference or to prevent "bottoming out" of the bladder or bag.

Referring to FIG. 3B, the design of the ribbing in the bladder or bag may be such that it focuses the incident waves. As shown in FIG. 3B, the split "U" shape works to force incident wave that flows heading away from the pressure sensor to curl around the bag and be directed toward the sensor. In either of the embodiments of FIGS. 3A and 3B.

Such a device may be embodied as a pad to be placed in the crib, as part of the mattress pad, or as part of the mattress itself. If placed under the mattress, additional structural support may be required FIGS. 4A-4D illustrate several embodiments of an air or fluid-filled pad sensor 10, shown from the side (beneath an infant 100) and from the top. FIG. 4A illustrates a single chamber pad sensor. FIGS. 4A-4C show different configurations of multiple chamber pad sensors, where lines or a grid indicate the separate chambers. Each chamber may be connected to a separate pressure sensor or multiple chambers may be connected to a single pressure sensor (not shown). The dark ovals in each panel represent conventional structures within the mattress. The pad may include any number of ribs, which may be part of the individual chambers. In some embodiments, the pad includes a single chamber. In other embodiments, the pad includes at least two chambers. In related embodiments, the pad includes a plurality of chambers. Where the pad sensor includes a plurality of chambers, the chambers may be vertically or horizontally stacked. The subject may rest on a stack of chambers or may rest on several adjacent chambers.

FIG. 5 illustrates and embodiment that employs an air or fluid-filled pad 10 for monitoring a subject's 100 cardiac and/or respiratory function and an ambient null sensor device 50 for monitoring ambient motion in the vicinity of the subject 100. The air or fluid-filled pad 10 and ambient null device 50 are separately connected to pressure sensors 30, 31, which provide pressure data for filtering and analysis by a microprocessor 200. The air or fluid pump 20 for filing the pad sensor 10 is indicated. The same or a different pump 20 may be connected to the ambient null device 50 (not shown).

Where an ambient and null device/sensor is used in combination with a pad sensor, the signal from the null device may be subtracted from (i.e., used to "null" or "cancel out") the signal from the pad sensor, allowing background signal (i.e., noise) subtraction.

In some embodiments, the pad sensor is filed with air. In related embodiments, the pad sensor is filled with an inert gas. In other embodiments, the pad is filled with a fluid. In particular embodiments, the fluid is an aqueous solution or water, optionally with an additive to retard the growth of microorganisms. Preferred fluids are inexpensive and non-toxic. Air-fluid emulsions or hybrid air/fluid configurations should produce similar results.

Pad sensors may be made of virtually any conventional material that is air or water-tight, as required by the particular embodiment. Exemplary materials include but are not limited to plastic (e.g., polyethylene, polypropylene, latex, vinyl, etc.) and fabric (e.g., canvas). Fabrics may be treated with a plastic or other coating to make them air or fluid-tight, as required. The pad may be covered for comfort or protection, so long as the covering does not substantially insulate the sensor from the vibrations generated by the subjects heart and/or lung function.

Where the pad sensor includes multiple chambers (e.g., FIGS. 4B-4D), each chamber may be operably connected to a separate pressure sensor or a plurality of chambers may be connected to a single pressure sensor. Generally, one pad is used for each subject. Where a single pad is used to monitor a plurality of subjects, e.g., as in the case of a large pad for monitoring a plurality of infants or adults, a plurality of chambers is preferred, thereby allowing distinction between the heart and respiratory functions of each subject on the mattress sensor.

The pad may include foam or ribbing to provide structural support, to reduce resonance or harmonics, or to preventing "bottoming out" under the weight of the subject. Foam may also allow for self-inflating of the pad. Ribbing may be the result of compartmentalization or chambers, as described above. Ribbing may also be used to focus the incident waves on the pressure sensor. In some embodiments, the pad sensor is in the form of a "U" shape to force incident waves to the ends of the tube, where the pressure sensor is typically located, as shown in FIG. 3B.

While changes in the dynamic pressure in the pad are used to monitor cardiopulmonary health status data (i.e., vital signs), static pressure in the pad sensor can be used to measure a subject's weight. In this manner, the pad sensor can also be used to provide weight data (e.g., over time), or to detect the presence or absence of the subject on the pad.

B. Other Sensor Embodiments

Embodiments of the present invention include motion sensors of various kinds and implementations for detection and quantitative measurements of vibration and movement and sounds that are appropriate for determination of (1) the subtle bodily movements associated with cardiac activity and the movement of blood within the body, (2) the movements associated with respiration, as well as (3) the simple presence of a subject and (4) major bodily movements made by the subject, such as shifting, rolling, moving arms, legs, trunk, and/or head. For example, in one aspect the instant system focuses on the ballistocardiographic measurement of movements of the first kind, the subtle movements associated with cardiac activity.

Fiber Optic

Figure 6:
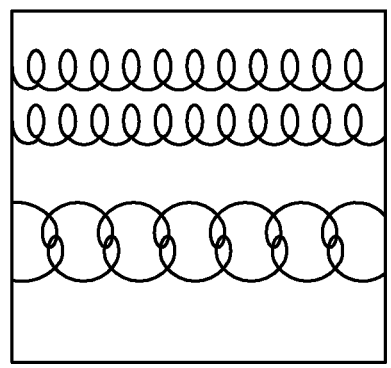
FIG. 6 is a diagram illustrating an alternative embodiment of the pad sensing unit used in the systems and methods shown in FIGS. 2 and 3, in which fiber optic strands are employed to detect a signal indicative of a vital sign.

Referring now to FIG. 6, some embodiments of the apparatus make use of fiber optic strands woven into the mattress pad, a blanket, or the mattress itself. Flexing the strands varies the intensity or absorption and/or polarization of the light passing through the strands. The strands can be curled near the critical radius to increase sensitivity. Overlapping the coils can also provide additional attenuation points. The output of the strands can be measured individually, or can be combined via a diffraction grating, and the resulting interference pattern can be measured at one or more points.

Resistive Mesh

Figure 7:
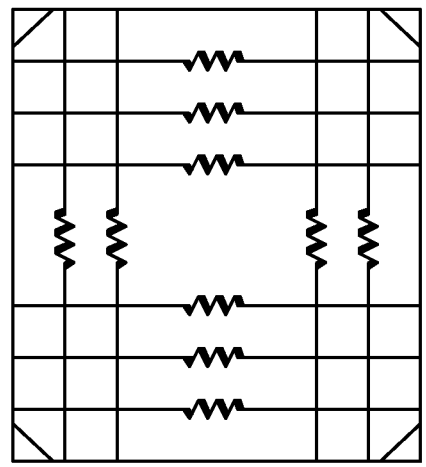
FIG. 7 is a diagram illustrating an alternative embodiment of the pad sensing unit used in the systems and methods shown in FIGS. 2 and 3, in which a resistive mesh is employed to detect a signal indicative of a vital signs.

Referring now to FIG. 7, some embodiments of the apparatus make use of a mesh of resistive elements stretched across the inside of the mattress or mattress pad that creates a method of sensing motion via changing resistance. The individual elements can be sampled, or they can be wired such that they create a vector. The resistors may be transduced by piezoelectric or by strain gauge sensors. The mesh may also be designed along the lines of resistive PDA touch screens.

In other embodiments, a pressure system consists of a strain gauge mounted on the surface of a mat that senses stretching of the surface when it is under a load. The mat may take various forms. In some embodiments, for example, a simple "air mattress" with an air pump at a remote location, with a manual pump included, or a "self-inflating" type of mattress, wherein foam blocks expand to draw in air, included, as would be known to artisans.

Capacitive Mesh

Figure 8:
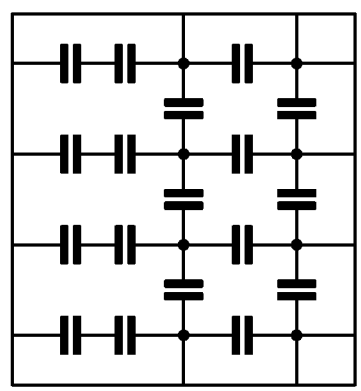
FIG. 8 is a diagram illustrating an alternative embodiment of the pad sensing unit used in the systems and methods shown in FIGS. 2 and 3, in which a capacitive mesh is employed to detect a signal indicative of a vital sign.

Referring now to FIG. 8, some embodiments of the apparatus make use of a resistive mesh, as above, but contain instead, capacitive elements strung across the mesh, as those skilled understand this to be merely illustrative, and not limiting of the present invention.

Suspended Particles

Figure 9:
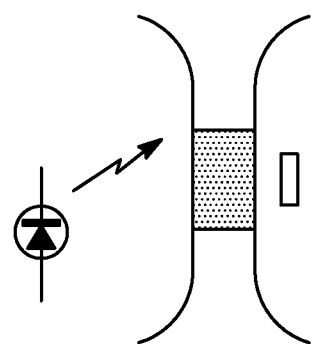
FIG. 9 is a diagram illustrating an alternative embodiment of the pad sensing unit used in the systems and methods shown in FIGS. 2 and 3, in which suspended particles are employed to detect a signal indicative of a vital signs.

Referring now to FIG. 9, some embodiments of the apparatus exploit the use of suspended particles within the interior material that are passed through a photo-detector. The relative density of these particles is a function of pressure; such density may be determined either by counting the number of interruptions across the photo-detector, or by measuring the change in the integrated light intensity. The lighting source can be of any appropriate wavelength, including in the visible, JR, or UV, ranges. The light source may be an LED, EL, etc. Using an optical mouse sensor may provide acceleration information as well. A variation on that theme is to use a liquid whose translucency is changed by pressure.

Electric Field

Some embodiments of the apparatus exploit the use of any of several different non-contact e-field sensors now available. Sensing the motion of the body by changes in the fields will provide data. The sensors can, again, be part of the mattress, the pad, etc. or as discussed arrayed at various places.

Ultrasonic

Figure 10:
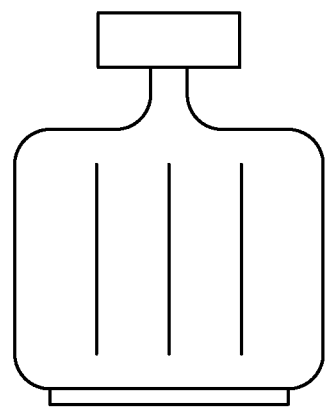
FIG. 10 is a diagram illustrating an alternative embodiment of the pad sensing unit used in the systems and methods shown in FIGS. 2 and 3, in which an ultrasonic transmitter is employed to detect a signal indicative of a vital sign.

Referring now also to FIG. 10, some embodiments of the apparatus make use of an ultrasonic transmitter and transducer, changing in the amplitude, the frequency (via Doppler), or interference patterns can be used.

Ultrawide Band

Referring now also to FIG. 10, some embodiments of the apparatus make use of an ultrawide band microwave transmitter and transducer, changing in the amplitude, the frequency (via Doppler), or interference patterns can be used.

RF communication to an embedded medical device such as a Pacemaker, Blood Pressure sensor or Glucose monitor, is likewise expressly contemplated by the instant teachings. Based on rules the device would trigger an action from one or more of the embedded devices, as would be known to artisans and readily linked to the present invention.

Visual or IR Video

Capturing visual or IR video and performing a motion algorithm to determine movement, is also compatible with an inherent in the instant platform. Also the IR sensor can detect subject's temperature, as discussed.

Optical Interference

Figure 11:
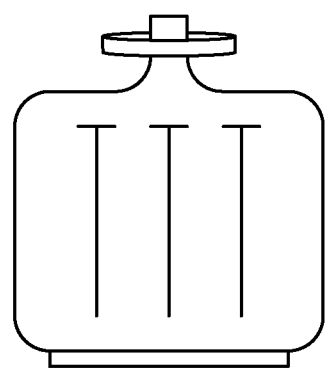
FIG. 11 is a diagram illustrating an alternative embodiment of the pad sensing unit used in the systems and methods shown in FIGS. 2 and 3, in which optical interference is employed to detect a signal indicative of a vital sign.

Referring now to FIG. 11, some embodiments of the apparatus make use of an LED array at one end which shines multiple beams of light through the medium, which is channeled. The resulting beams are passed through a diffraction grating, and the interference pattern is then measured (FIG. 11). A variation is to place a fiber optic strand at the end of each channel, and use that to focus for the grating.

Further appropriate is a magnetic field sensor using magnets on edges of platform suspended in an polymer influencing hall effect sensors or coil sensors. Sensors likewise can be load cells included in legs of crib or bed, or mounted on springs that hold mattress. Careful control of mattress material is required. Also, frame holding mattress could be suspended within bed frame with sensors on each axis Mechanical Plate Embodiment In some embodiments, the cardiac and respiratory functions are monitored using a mechanical plate (or electromechanical) sensor. In a particular embodiment, the plate sensor includes at least one weighted strain gauge for detecting vibrations resulting from cardiac and/or respiratory functions of a subject.

An embodiment of the method and apparatus that employs a strain gauge is shown in FIGS. 12A and 12B. As shown in FIG. 12A, the plate sensor apparatus comprises an upper plate 60 and lower plate 61. The subject 100 rests on the upper plate 60. As shown in FIG. 12B, the upper and lower plates are connected via one or more strain gauges 71, 72, 73, 74, each having a first end 62 attached to the upper plate 60 and a second end 63 attached to the lower plate 61. The strain gauges may be adapted to measure strain in any dimension, such as the X, Y, and Z, axes as shown in FIG. 12B. Strain gauges may also measure the rotation of one plate with respect to the other, the tilting of one plate with respect to the other, or the flexing of the upper or lower plate.

Ballistic movement of the subject in response to heart and lung function is generally not limited to a single direction. In some embodiments, it may be desirable to monitor movement in several directions to increase the sensitivity of the plate sensor. However, it is generally not necessary to monitor movement in all directions. In some embodiments, it may be adequate to monitor movement in one direction. Thus a limited small number of strain gauges, such as 1, 2, 3, 4, 5, or 6 should be sufficient to detect cardiac and/or lung function. The two plates may further be connected by springs, foam, an air or fluid-filled bag or cushion, etc. to maintain a nominal separation distance between the plates. The weight of the intended subject will be reflected in the springs, foam, or other material used to maintain distance between the plates.

Figure 13:
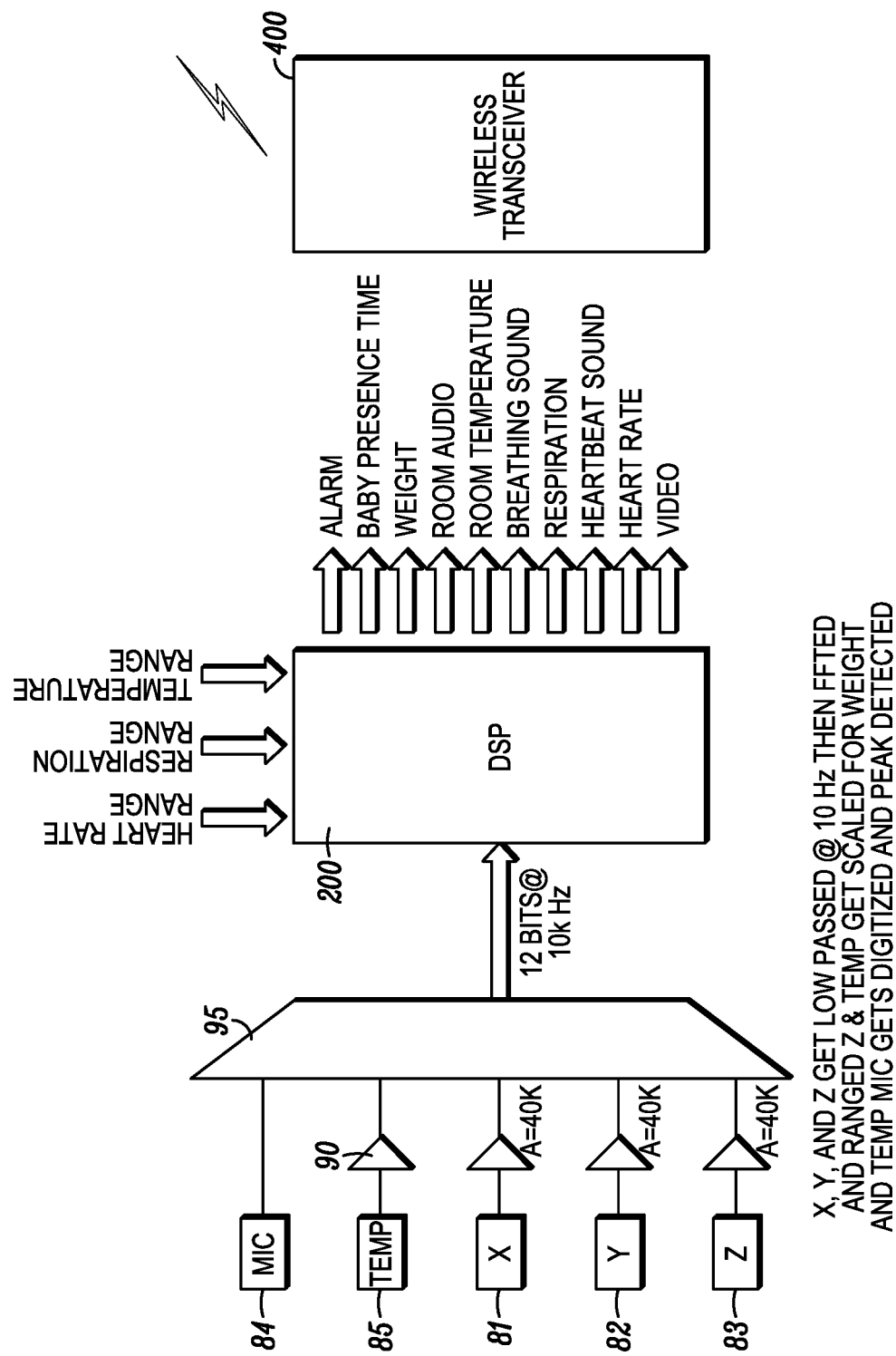
FIG. 13 is a diagram illustrating a system and method for processing data generated by the mechanical sensor shown in FIGS. 12A and 12B.

FIG. 13 is a schematic diagram showing how an electromechanical sensor is used according to the method and apparatus. Electrical signals from strain gauges or pressure sensors measuring movement in the X 81, Y 82, and Z 83 axes, along with (optionally) electrical signals from other sensors, such as a microphone 84 and temperature gauge 85 are fed into filters 90, received by an analog to digital converter 95, or similar device, and analyzed by a digital signal processor (DSP) 200. The DSP includes preselected or learned/trained parameter information (arrows pointing down towards DSP 200) and may trigger one or more events (arrows point away from DSP 200). The DSP 200 may also communicate with a wireless transceiver 400 for further distributing the processed signal.

C. Further Embodiments

Combinations of gas/fluid pressure sensors and strain gauges may be used to increase the sensitivity of detection of vibrations resulting from heart and lung function. In addition, other types of sensors may be used in addition to, or in place of, gas/fluid-filled and electromechanical sensors. Cost and practicality should be considered in the design. The above-described sensors offer adequate sensitivity without being overly elaborate in design.

Although preferred health status sensors are non-invasive, non-entangling, and unobtrusive, some embodiments employ a sensor that is worn or attached to the subject, e.g., in the form of a wrist or ankle-worn sensor. Such sensors may be adapted to communicate with a processing or analytical device in a wireless manner, thereby minimizing the intrusive nature of the sensor.

III. Additional Sensors

In addition to the pad or plate sensor for detecting vibrations from heart function and/or breathing, the method and apparatus may include one or more additional sensors for obtaining health status or environmental data. Such additional sensors include but are not limited to temperature sensors for monitoring ambient temperature and/or the temperature of the subject; light sensors for monitoring ambient light; weight sensors for measuring subject weight, moisture sensors for detecting bed-wetting or other nocturnal emissions; audio and/or video sensors for detecting crying, fussing/complaining, snoring, tossing and turning, position indicators for detecting changes in mattress angle, changes in the subjects orientation, etc.

Exemplary additional sensors include microphones, cameras, thermometers, photoelectric devices, microelectromechanical sensors (MEMS), sphygmomanometers, strain gauges, accelerometers, inclinometers, altimeters, barometers, radiation detectors, moisture gauges, and the like. In some embodiments, the additional sensors obtain data in a non-invasive manner, much like the pad sensor. In other embodiments, the additional sensors are connected to the subject. Data from such additional sensors can be used passively, i.e. recorded for later use; sent periodically to web pages or cell phones; displayed on a monitor, etc. Data from such devices can also be used actively, i.e. used to determine ambient light, detect motion via frame differencing, triggering an alarm, etc. Exemplary additional sensors are exemplified, below:

A. Ambient Light Monitors

Ambient light monitors (photo detectors, photo diodes, CCD integrators, etc.) can be used to capture and track the amount of light in the room occupied by the subject. By looking at the spectral components, it is also possible to determine if the source is natural or artificial light.

B. Video Capture Device

Video capture devices, such as visible-light or infrared (J R) cameras, can be used to take snapshots, time lapse images, or continual frames of the subject. In some embodiments, data from a video capture device is used to trigger a wake-up alarm, turn on or off lights, etc. Data from an infrared detector may be used to monitor the temperature of a subject. Video data may also be used to determine the position of a person or animal, as well as when the person/animal has turned over.

C. Audio Sensors

Audio sensors, such as microphones, can be used to identify crying, coughing, snoring, screaming, hiccoughing, groaning, and/or "fussiness." Microphones are well known in the art.

D. Temperature Sensors

Temperature/thermal/JR sensors can be used to monitor ambient room temperature and/or a subject's body temperature. Where the temperature sensor measure a subject's temperature, it may be placed on the top of the mattress sensor or built into the pad or plate sensor. Non-contact thermometers are particularly useful for measuring a subject's body temperature.

E. Chemical Sensors

Chemical sensors can be used for warning and/or diagnosis. For example, carbon monoxide, carbon dioxide, oxygen, natural gas, methane, hydrogen sulfide, and ammonia sensors can be used to identify life threatening environmental conditions caused by, e.g., poor ventilation, smoke, fire, etc. Chemical sensors may also be used to monitor flatulence or metabolic conditions that result in the production of detectable chemical species (e.g., ketosis, trimethylaminuria). A carbon dioxide sensor may be utilized to determine if an infant has rolled over onto its front, a potential condition for suffocation. A vast number of chemical sensors are available, depending on the chemicals likely to be present in the particular environment.

F. Weight Sensors

In some embodiments, it may be desirable to monitor a subject's body weight in addition to the subject's cardiac and/or respiratory function. Body weight monitoring is readily accomplished using a conventional scale, which is typically placed under the mattress sensor.

Body weight may also be determined from the average (i.e., static as opposed to dynamic) pressure in the pad sensor or on the plate sensor, which corresponds to the weight of the subject. In this manner, the pad or plate sensor may serve as both a cardiac function/breathing monitor and a weight sensor (or scale).

G. EKG/EEG

Electrocardiographs (EKG; ECG) may be used to supplement data from the pad sensor, to calibrate the pad sensor, or to detect particular cardiac abnormalities.

In some embodiments, electroencephalograph (EEG) data is obtained from a subject to monitor brainwaves. This embodiment is particularly useful for studying sleep patterns in subjects and for monitoring subjects for brain activity following a stroke, heart attach, or trauma.

H. Movement Sensors

In some embodiments, movement (or motion) sensors are used in combination with the pad or plate sensor to detect the presence of the subject in the room, to determine whether a crib, bed, chair, sofa, etc. is occupied, to monitor gross subject movements. Movement sensors include inclinometers, accelerometrs, photodetectors, and the like.

IV. Ambient Null Sensor Device

In some embodiments, the pad or plate sensor is used in combination with an ambient (or null) sensor device for measuring ambient motion in the vicinity of the subject. In preferred embodiments, the ambient null device is similar to the pad or plate sensor for monitoring cardiopulmonary vibrations, differing in that the subject does not rest on the ambient null sensor. In other embodiments, the ambient null device is a device different from the pad or plate sensor, including but not limited to an accelerometer or bob weight device.

The ambient null device is used as a "control" for environmental changes that are not due to movement of the subject in question. The signal/data from the ambient null sensor can be subtracted from that of the pad or plate sensor to reduce background noise and account for changes in the environment in which the subject is resting on the pad or plate sensor.

In preferred embodiments, the ambient null device incorporates a sensor similar to that of the pad or plate sensor, such that the data produced are comparable. In some embodiments, the sensor is of the same type or model. Alternatively, the ambient null sensor is of a different type that the pad or plate sensor, including any of the sensor types described herein.

Not all embodiments of the present method and apparatus require use of an ambient null device/sensor. Vibrations resulting from heart function and breathing are regular and rhythmic and not easily confused with ambient noise; therefore, it should generally not be necessary to use an ambient sensor device unless suitable analog or digital filters, including software filters, cannot be designed. Ambient null devices are generally only required where background noise (including noise from other human or animal subjects) interferes with detection and monitoring of cardiac function and/or respiration.

V. Data Processing

Raw data from a pad or plate sensing unit and, optionally, other sensor(s) and inputs, are processed to produce processed data. Processing may be by analog means or by digital means.

Figure 14:
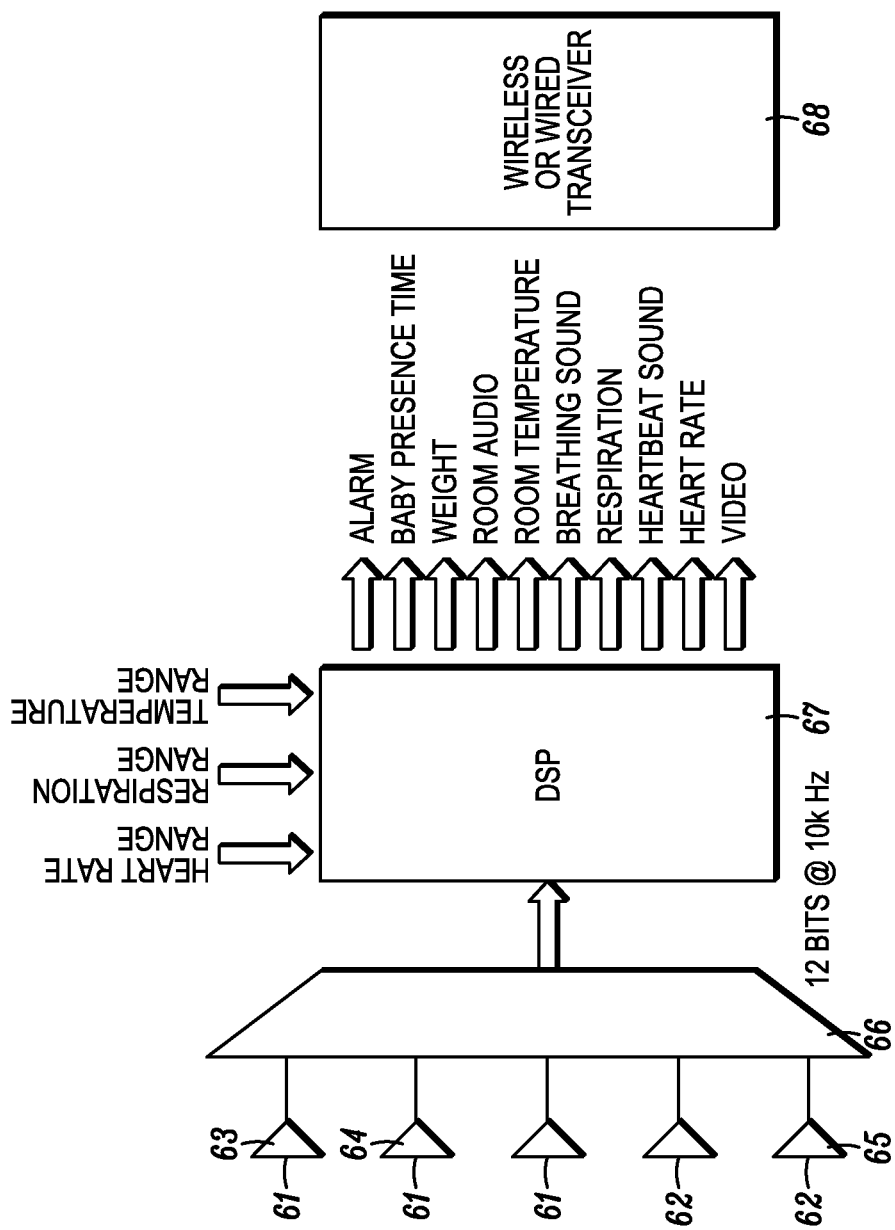
FIG. 14 is a diagram illustrating a system and method for monitoring vital signs in which data generated by multiple sensors are analyzed by a DSP and used to trigger events.

FIG. 14 shows a typical data processing arrangement. Input data from, e.g., one or more pressure sensors or strain gauges 61 and optional additional sensors 62 are filtered using band-pass filters 63, 64, 65, amplified, and digitized, e.g., using an analog to digital converter 66. The filtered signals are then sent to a DSP 67 for further processing and/or analysis. The DSP 67 may trigger alerts, alarms, or events directly and/or may be sent to a remote location using a wireless transceiver 68. The remote location may be, e.g., the internet or a remote monitor. In other embodiments, input data is first digitized and then filtered or otherwise processed. Data from different sensors may be processed differently.

Figure 15:
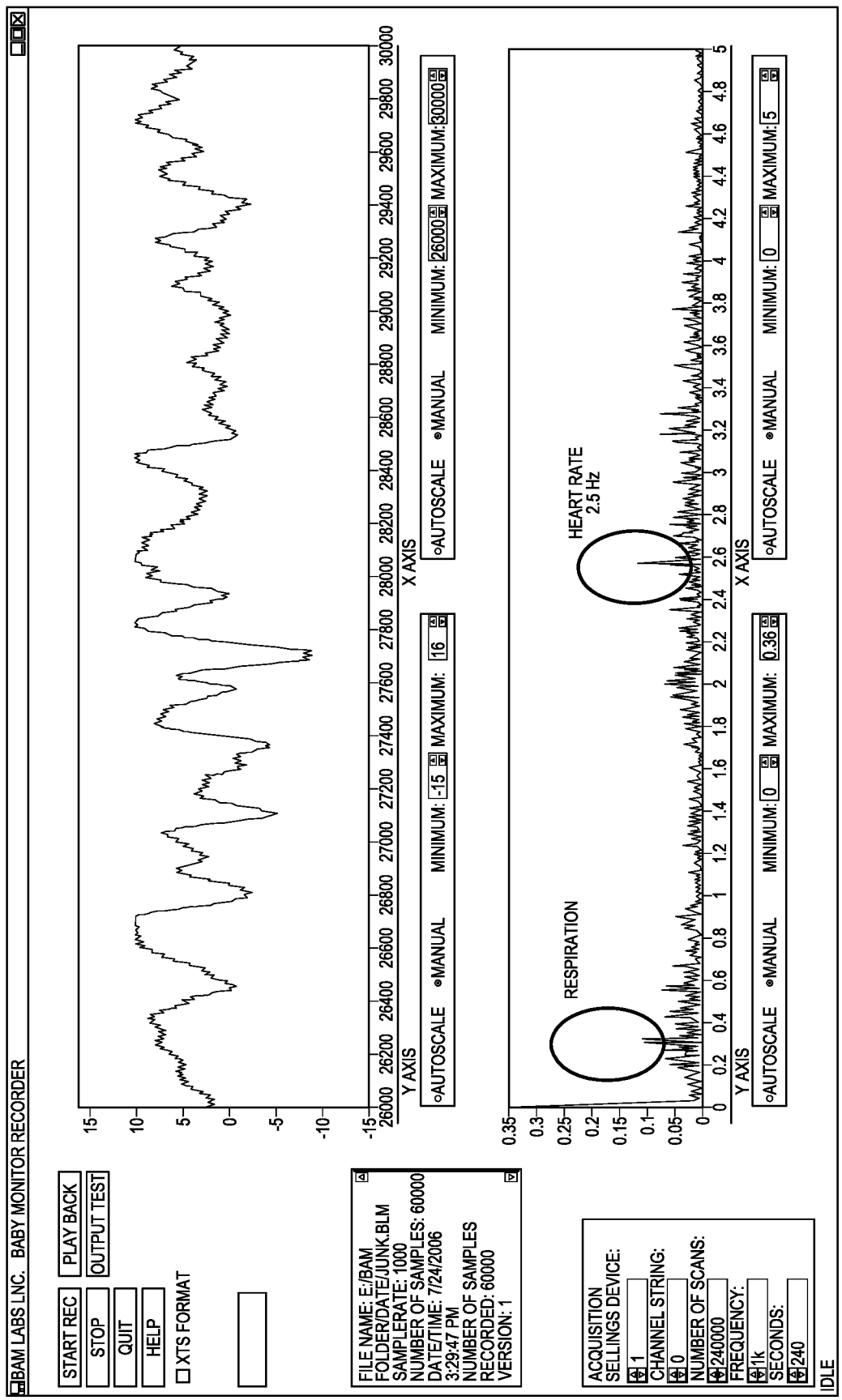
FIG. 15 shows an example of processed data generated by the sensors of FIGS. 1-13 using a 6-month-old infant subject.

FIG. 15 shows exemplary cardiopulmonary data obtained from an infant placed on a pad sensing unit as described. The raw sensor data were processed through a 10 Hz low-pass filter, amplified, digitized, digitally band-passed, and then fed to a fast Fourier transformer to convert the data to the frequency domain. Similar results could have been obtained by amplifying and digitizing the raw signal and using a digital/software low-pass filter. Since the beating frequency of a human heart is approximately 50-200 beats per minute (0.83-3.33 Hz) the frequency range of interest for monitoring human (and many other animal) heart rates is from about 0.1 to about 10 Hz, or from about 1 to about 5 Hz, or even from about 2 to about 5 Hz. Since the respiration/breathing frequency of a human is about 10-20 breaths per minute (0.16-0.33 Hz) the frequency range of interest for monitoring human (and many other animal) breathing rates is from about 0.1 to about 1 Hz but generally less than about 1 Hz.

Analog and/or digital filters can be used to select any portion of a signal for analysis. Other frequency ranges may be of interest, e.g., for monitoring coughing, screaming, hiccoughing, snoring, groaning, turning, flipping, shivering, shaking, convulsions, movements in dreams, erotic stimulation, or other movement.

Processed data can be analyzed by a microprocessor and used to trigger an event or event set, such as alerting medical professionals to assist in identifying, preventing, or treating the subject, sounding an alarm, etc, as described. The event set that is triggered depends on the rules created or tailored by the user. Examples include sending a message via the internet, logging an entry in a log file, changing a database entry, and the like. Data can also be recorded, with or without accompanying analysis, for later reviewed.

The present method and apparatus are ideally integrated with internet/web-based services, wireless telecommunications, advanced audio and video processing, instant messaging, digital and analog signal processing, medical record databases and patient records, and private and public health agencies.

Where the method and apparatus are connected to the internet, filters and/or microprocessors used to process raw data and/or analyze processed data may be at a location remote from the sensing unit. In one embodiment, raw data are transmitted via an internet connection to a microprocessor associated with a server. In another embodiment, data processed by a local microprocessor are transmitted via an internet connection to a microprocessor associated with a server.

VI. External Devices and Platforms

The present invention leverages existing and prospective technology for data processing and analysis, and data coming from the various sensors, such combinations of data can be used to profile the subject as known to artisans. Such profiles may be created or tailored by a qualified user, and may be used to elicit alerts or alarms; they may also be flagged as "unusual" events, to draw the attention of a user, a researcher for example, who may be reviewing historical data.

In some embodiments, it may be desirable to use in the present method and apparatus in combination with an external device or platform, such as a text messaging platform, data logger, printer, alarm system, alert siren, or other data acquisition or actuating device; or a computer (i.e., microprocessor) capable of performing analytical functions.

In some embodiments a message platform is used for delivery of data, messages, alarms, and alerts. These messages may take, for example, the form of text messages (short message service, SMS) sent by way of telephone services, email, voice calls, and in home monitoring media including audio, video, and heart and breathing sounds, either in the form of direct audio, or simulated sound processes. Telephone services utilized by embodiments of the invention may include either or both the public switch telephone network (PSTN) connections and cellular telephone connections as well as a IP network connection.

Alarms or alerts may be triggered by processed signal data that are outside normal values or meet pre-selected user trigger points. Such alarms or alerts may be delivered by a telephone, web, or other service, as described. Alarms or alerts may be sent to e.g., pre-selected health care professionals (including paramedics, physicians, nurses, police, and the like), relatives and/or guardians, public health agencies, child services, etc., as determined by the user. Simple alarms or alerts are audible and/or visible signals, such as horns, buzzers, sirens, lights, and the like. In the case of an alert, it may be necessary to stimulate the patient, either with audio, vibration, light, smell, motion, medication or defibrillation.

Alarms, alerts, and/or panic signals may also be localized to particular places in a home, hospital, elderly, care facility, or infant care facility. Such signals may transmitted by wired or wireless technology, such as cabling, WiFi, Zigbee, Bluetooth, etc., for contacting receiving devices such as cell phones or personal digital assistants (PDAs).

Some embodiments may also include a "panic button" that can be manually activated by the subject or another person. The panic button may cause a signal to be sent to pre-selected health care professionals, relatives and/or guardians, public health agencies, child services, etc., as above. As above, the signal can be sent via a telephone, the web, or another service, as described.

In some cases, it may be desirable to trigger an automatic action in response to processed data. For example, it may be desirable to disturb a subject's sleep with an audible and/or visible signal or through vibration, shaking, or physical contact with the subject. In other embodiments, pre-selected health status data causes, e.g., medication to be dispensed to a patient, a respirator to begin pumping air, a defibrillator to restart a subject's heart, a portion of a mattress to be raised or lowered, etc.

In some embodiments, the external device is a data logger or recording device for keep track of a subject's health status data. In other embodiments, a printer of chart recorder is connected. Most any of the described external devices can be used in combination.

Figure 16:
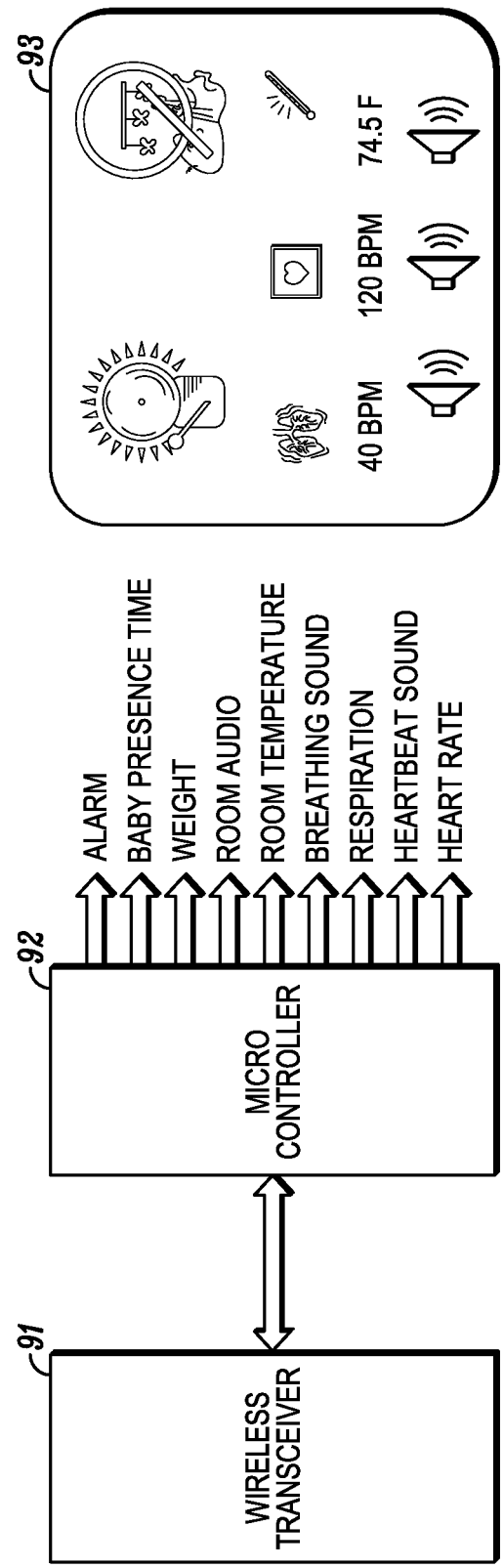
FIG. 16 is a diagram illustrating a system and method for monitoring vital signs including a wireless transceiver receiving data from a mattress sensor to communicate with a remote microcontroller for monitoring and responding to health status data.

FIG. 16 shows an exemplary system in which data from a pad or plate sensor (and optional additional sensors) is communicated to a microcontroller 92 via a wireless transceiver 91. The microcontroller 92 analyzes the data, which may be viewed or presented on a remote monitoring device 93, in addition to being sent to the internet, being used to trigger event sets, etc. The remote monitoring device could be located, for example, in a physician's office, a nurse's station, a fire department or paramedic station, a parent's or guardian's bedroom, etc.

In all cases, the method and apparatus make include two-way (or more) communication between subject and a remote monitoring location. The two-way communication may be audio, e.g., using microphones and speakers; video, e.g., using cameras and monitors; or text, e.g., using email, messaging, or the like.

VII. Internet Connectivity

Embodiments of the method and apparatus include a web portal, as part of the monitoring capability. The web portal is supported by a web server through which users may access the web. Connection to a web portal also provides access to a back-end server to capture, store, and analyze data from the various sensors of the system. The web portal typically includes an interface for the user to set various pre-selected parameters, such as which data triggering alerts or alarms.

In some embodiments, the interface provides access to a user's account (typically the subject's account), where preferences are pre-selected, and where billing and management are handled. The interface may further provide storage, presentation, and delivery of data that have been recorded. The data may be annotated with, for example summaries and analyses. The web portal may further provide drug recommendations, advertising material, news, tips, or other information based on health status data collected from the subject.

In some embodiments, the interface to the web-based service further provides storage, presentation and delivery of data that have been captured, with, for example summaries and analysis, for example charts of a baby's weight and other data over time, apnea events, to caregivers, healthcare professionals, or researchers. The web-based service may further provide advertising, context sensitive advertising based on stored data, information, video, audio, images or news space from third party providers. Additionally, embodiments of the web-based service may include blogging and chat services for users to publish text, audio, and video to communicate with other users.

Connectivity to the internet and/or local area networks permits the pad or plate (or additional) sensors of the present method and devices to be linked to patient/invalid monitoring devices, alert services, and web applications for transmitting, receiving, and storing health data. In particular embodiments, the method and device are used to provide alerts or alarms in response to an adverse cardiovascular or respiratory event. Alerts generated by the system may be directed to health care professionals, family members, to a data logging device, or to emergency service agencies such at police, fire, ambulance, medic, etc.

In some embodiments, a web-based service specifically designed to monitor a plurality of subject using separate pad or plate sensors, is provided. The subjects may be in different locations. The web service may analyze data and determine a course of action, which can include any of the alerts, alarms, or events described.

VIII. Patient Populations and Settings

The foregoing methods and apparatuses provide a method and apparatus for the non-invasive, non-entangling, and unobtrusive health status monitoring of a subject in a home or health care institutional setting, particularly with respect cardiovascular health status. A healthcare institutional setting may be a physician's office, hospital, clinic, nursing facility, veterinary clinic, or assisted living facility, by way of examples.

At least three classes of people can be helped by the foregoing methods and apparatuses: (1) the individual who is being monitored, in which case engagement can be passive on the part of the individual, (2) one or more individuals caring for diagnosing or responsible for the subject being monitored, such individuals being capable of responding appropriately to an alert or signal from the methods or apparatuses that indicates an unusual event, and (3) individuals not necessarily or immediately involved in the care or monitoring of the subject, but who are using data, primarily at later time, for research or diagnostic or treatment or medical device development purposes.

The method and apparatus may be used to monitor "vital signs" or other health status data. As used herein, vital signs include but are not limited to respiratory (breathing) rate, the concentration of respired gases, pulse rate, blood pressure, and cardiac electrical activity.

Data monitored, collected and analyzed beyond basic vital signs may include other direct factors, including by way of example, temperature, ambient light, weight, audio, and video. Indirect and computed factors may include, for example, the detection of crying, fussing, and sleep state. Any of these factors may be stored and used to generate historical information such as, for example, sleep cycles, the chronology of weight gain or loss, and the chronology of time spent in bed.

In some embodiments, the method and apparatus may be used to monitor and thus protect the health and lives of infants at risk for the occurrence of sudden infant death syndrome (SIDS). However, those skilled in the art will recognize that method and apparatus are applicable to children, adolescents, adults, the elderly, senior, and animals. For example, adults considered at risk for sleep apnea or adverse cardiovascular events may be monitored using the present method and apparatus. Embodiments may be designed to protect individuals at rest, asleep, or untended. Humans or animals being monitored may be referred to as a "patient" or "subject," and may be of any age or health status.

The methods and apparatus may also be used to study dream behavior, to monitor a subject's bathroom usage or frequency of changing position in bed, to monitor the amount of time a subject spends in a bed chair, couch, etc, to monitor the frequency and/or severity of convulsions or apneas, to monitor the frequency and/or severity of arrhythmias, or to monitor a bed or other surface for evidence of erotic stimulation.

In addition, in some embodiments adults considered to be at risk for sleep apnea or adverse cardiovascular events are subjects that can be protected. Embodiments of the invention can protect such individuals at rest, asleep or generally alone or untended in an immediate sense. Likewise, those needing to have their data monitored on an ongoing basis can be monitored using the foregoing embodiments.

The methods and apparatus may also be used to determine whether a subject is present in a particular location. In this manner, health-status data may be used to identify a particular subject (e.g., via pattern recognition) to confirm the identity of the subject in the location. The health-status data may also be used only to indicate the presence of any subject in a particular location, e.g., to make sure a baby is in a crib, an elderly patient is in a bed, or a dog is in a kennel, without identifying the subject.

The foregoing embodiments can provide a non-invasive, non-entangling device to monitor heart rate. In one case, the device relies on arterial tomography techniques to determine the heart rate. The device incorporates a low frequency sensor to hear the blood pressure wave traversing the arm. This signal is digitized and analyzed locally and the results are transferred to the data storage wirelessly.

Applications of the foregoing embodiments also include the monitoring of subjects for more general or diagnostic purposes, when, for example it is determined that long term physiological monitoring of vital signs may be helpful in diagnosis of disease. Other embodiments of the invention include its use for tracking the time when a baby sitter is putting a monitored subject infant or child to bed, how long the subject is actually asleep, or how long the subject is active.

Embodiments of the invention include monitoring devices, alert services, and web applications for transmitting, receiving, and storing health data.

In other aspects, the invention is directed toward longer term analysis of physiological data for diagnosing disease and for medical research purposes. In these aspects, there is less involvement of alerts, alarms, and responding to acute events; there is, instead, greater direction toward chronological, geographical and environmental tracking of parameters, and analysis of interactions that may statistically emerge from correlating and comparing the various forms of data.

The system has enhancements to support deaf or blind users, in the case of blind users, the alerts and data will be communicated orally. In the case of deaf users the alerts and data will be transferred visually or by active vibrations.

IX Baby Monitor

An example of the application of the foregoing embodiments is a baby monitor illustrated in FIGS. 17-21. While this example shows the monitoring of the baby, the disclosed method and apparatus would be useful in monitoring other subjects as well, such as the infirm, elderly or animals.

Figure 17:
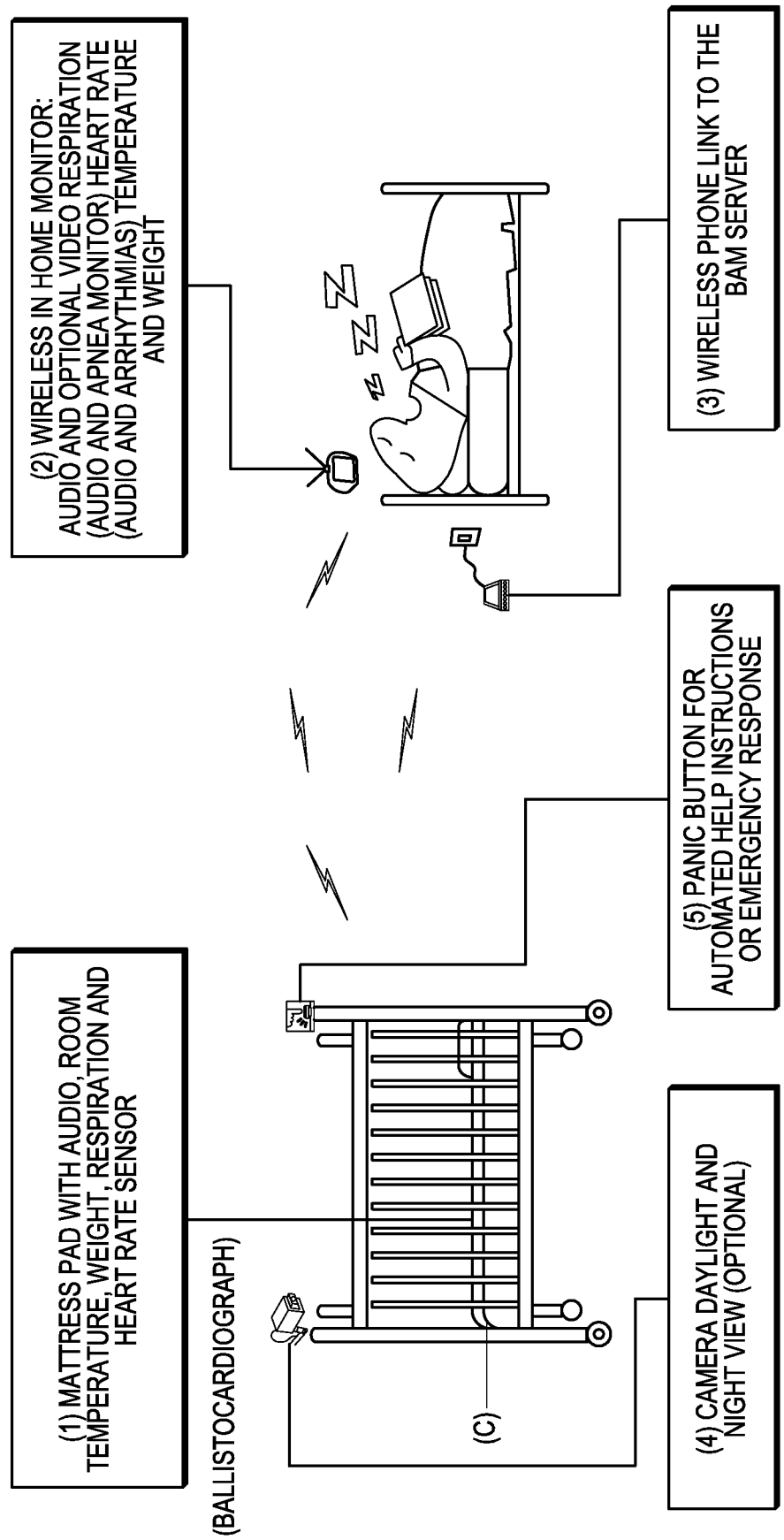
FIG. 17 is a diagram illustrating a baby monitor in accordance with another embodiment of the invention.

FIG. 17 depicts an embodiment of the invention which is configured to monitor a baby. A monitor-enabled mattress pad 1 is shown in a child's crib, which includes sensors enabled to measure and transmit data of various types, including audio data, room temperature, infant weight, respiration rate, and heart rate. Audio data is generated by a single or array microphone (not shown). Additionally, some embodiments include a camera 4, which may be configured to capture images in visible and Infrared light, including very low light situations. Some embodiments may include a so-called "panic button" 5 mounted on the crib, which a user (a parent or relative may activate for the purpose of obtaining the help of a third party). In addition, the Panic Button apparatus would speak directions to the patient and the caregiver, or dial the phone. Although some embodiments may include hard-wired data transmission, typically sensors and recording devices transmit data wirelessly. Such transmitted data are received on a wireless home monitor 2, which through a combination of audio and video, and screen displays is enabled to provide data, images, and sound to a user somewhere else in the home. Audio transmission is typically of respiration and heart beat sounds, but may also include straight audio from the location, which would pick up sounds of the infant or other ambient sound. As shown in the embodiment of FIG. 1, the monitor 2 can be in the bedroom of a parent; this is a typical location, but the home monitor may be located anywhere within the home, limited only by the range of the wired or wireless transmission system. The home monitor, itself, may be mobile, as for example, a personal digital assistant (PDA), notebook, laptop, or cell phone. The home monitor may also be relatively stationary, for example, a desktop computer. A wireless phone link 3 may also receive data, and may transmit data to an offsite server.

Figure 18:
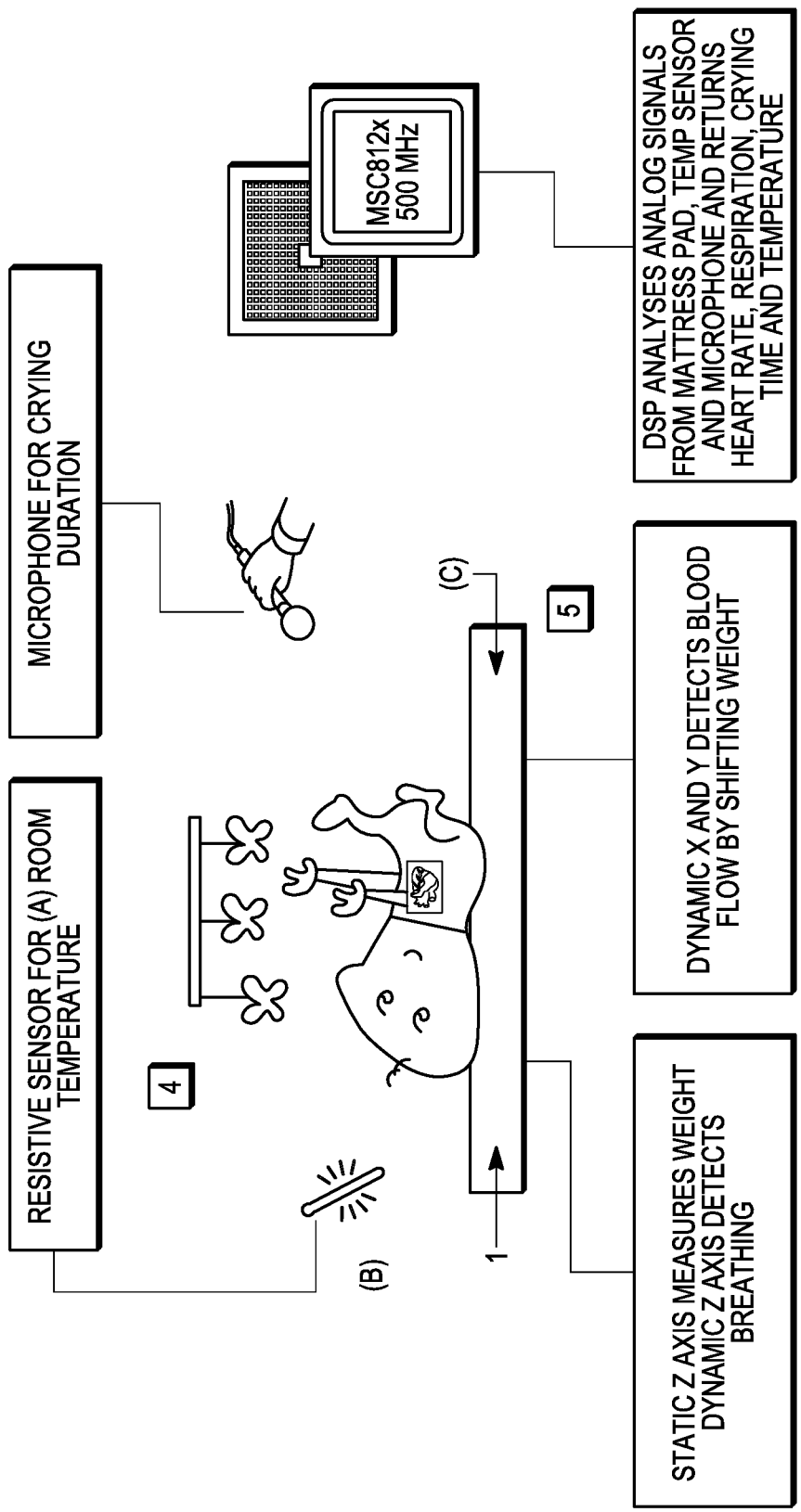
FIG. 18 is a diagram illustrating the handling of data generated by the baby monitor of FIG. 17.

FIG. 18 shows further detail regarding monitoring and the handling of data generated by a baby monitor embodiment of the inventive health monitoring system. Shown, for example, are a resistive sensor A for temperature measurement and a microphone B to capture crying. Other components of the system recognize "crying" and measure frequency and duration. Within or associated with the mattress pad is a ballistocardiograph device and a scale C. Data generated by these components may be combined into a three axis system, where the dynamics in the X and Y axes detects blood flow by way of shifting weight within the body of the infant. A static Z axis measures weight, and a dynamic Z axis detects breathing. These various data from sensors, microphones, and cameras, according to embodiments of the system, are transmitted, typically by wireless means, to a computer D for digital signal processing (DSP) analysis of the analog signals.

Figure 19:
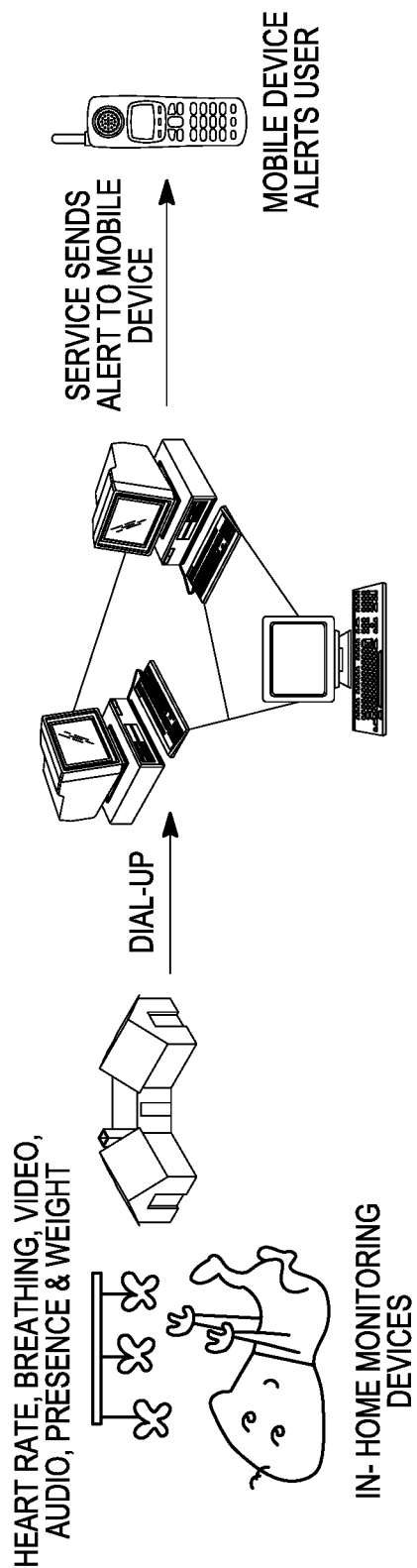
FIG. 19 is a diagram illustrating communications between baby monitor of FIG. 17 and a central server.
Figure 20:
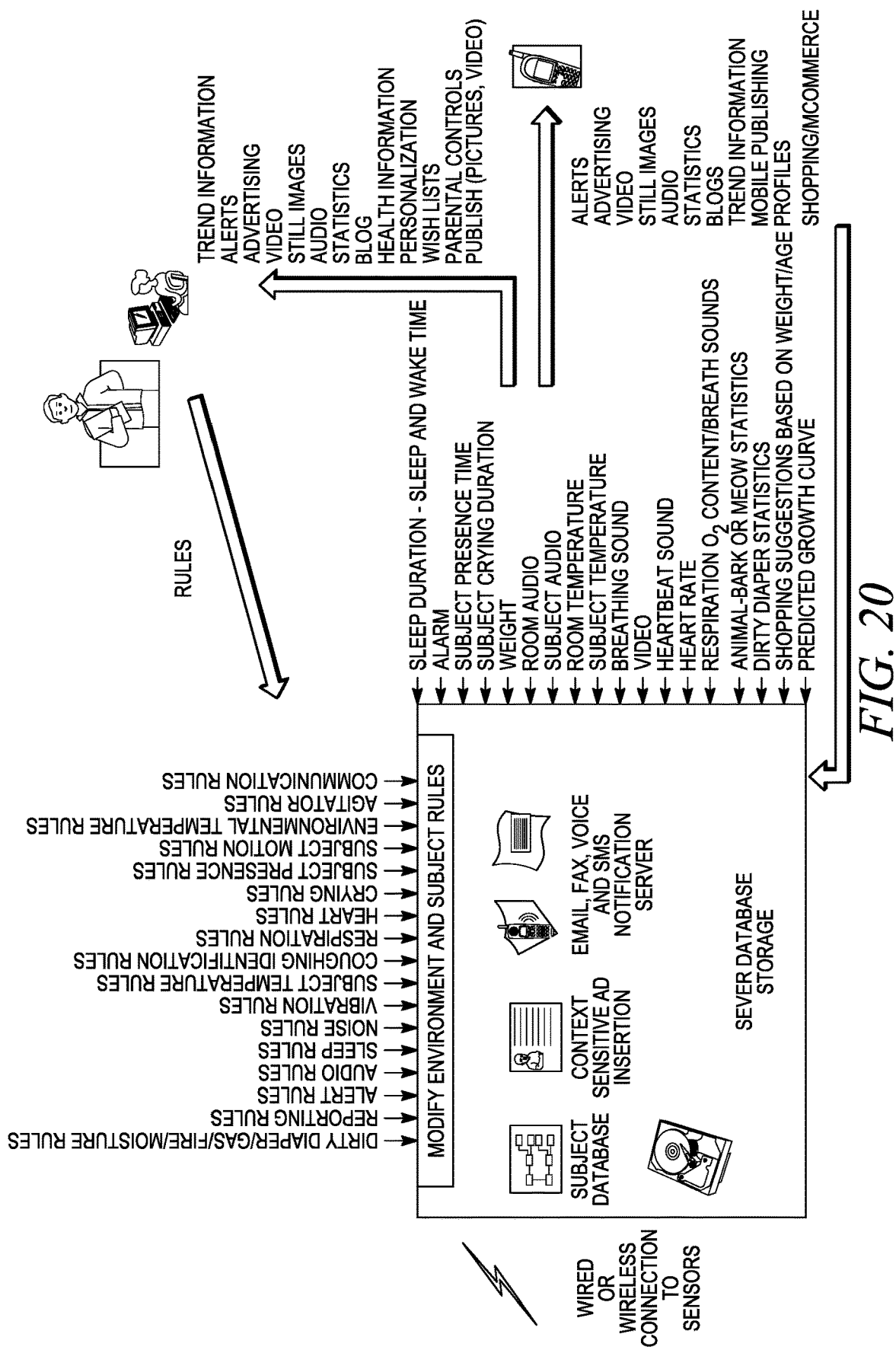
FIG. 20 is a diagram illustrating a set of rules, alerts, truth rules about predicates and data storage mapping elements that can be applied to the baby monitor of FIG. 17.
Figure 21:
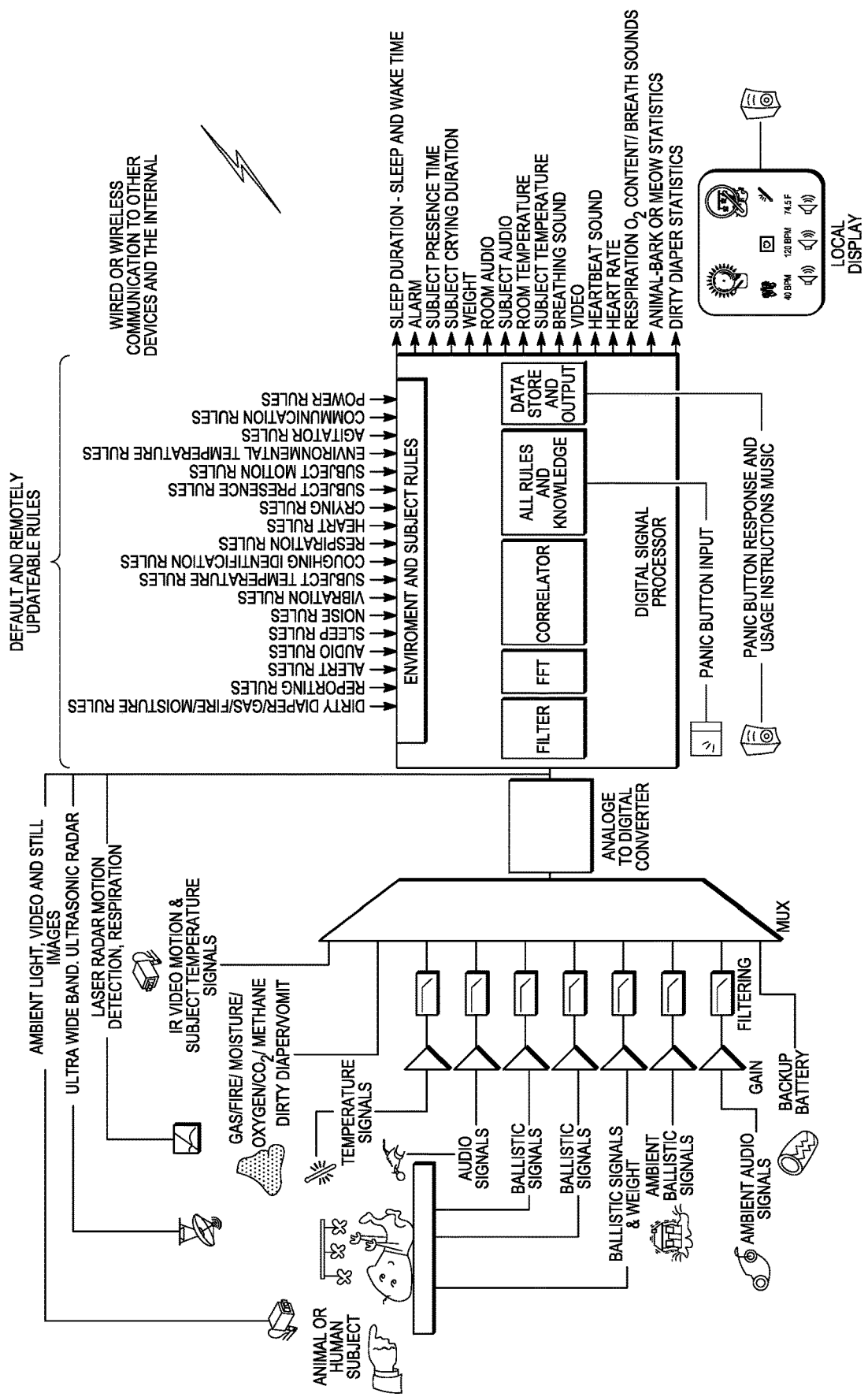
FIG. 21 is a diagram illustrating a set of rules and alerts that can be applied to the baby monitor of FIG. 17.

FIGS. 19-21 are further details and a schematic of details of the transmission and processing of data from a baby monitor. These details would be also applicable to an adult health monitor embodiment.

FIG. 19 illustrates the communications between baby monitor of FIG. 17 and a central server. The central server can send alerts to remote devices such as cellular telephones.

FIG. 20 and FIG. 21 are an illustrative set of rules, alerts, truth rules about predicates and data storage mapping elements that can be applied to the baby monitor of FIG. 17. FIG. 21 further illustrates integration of various system elements, in terms of default and remotely updateable rules, and wired and wireless connection. Those skilled in the art readily understand how such systems function and further detail is omitted.

Further embodiments and variation using the present method and apparatus will be apparent to the skilled artisan in view of the disclosure. The methods are apparatus are in no way limited by the description.

It is claimed:

1. A system for monitoring heart and respiration rates of a human subject at rest, comprising, in operative condition:
    a sensing unit having (i) a fluid or gas-filled pad adapted for use with a mattress or chair support, for cushioning at least an upper body portion of a subject lying on or resting against the mattress or chair support, and (ii) a pressure sensor in gas or fluid communication with gas or fluid in the fluid or gas-filled pad, for generating electrical signals in response to pressure variations within the fluid or gas in the pad;
    a first pump in fluid or gas communication with the fluid or gas filled pad for maintaining fluid or gas within the pad at a selected pressure or within a defined pressure range;
    an ambient-null device comprising a fluid or gas-filled ambient pad, a weight carried on the ambient pad, for exerting pressure thereon, and an ambient pressure sensor in fluid or gas communication with fluid in the ambient pad, for generating electrical signals in response to pressure changes within the fluid or gas, in response to ambient motion in the vicinity of the subject, wherein the fluid or gas-filled ambient pad is in fluid or gas communication with a second pump for filling the fluid or gas-filled ambient pad; and
    a monitoring unit operatively connected to the sensing unit and the ambient-null device, the monitoring unit configured to: (i) receive signals from the sensing unit and the ambient-null device, (ii) process signals received from the sensing unit and the ambient-null device to filter ambient motion from pressure variations indicated by signals received from the sensing unit, (iii) generate information about the heart and respiration rates of the subject using the signals received from the sensing unit that have been filtered to remove the ambient motion, and (iv) relay such information to a monitoring station or individual.

2. The system of claim 1, wherein the pressure sensor of the sensing unit and the ambient pressure sensor of the ambient-null device are the same type of sensor.

3. The system of claim 1, further comprising:
one or more movement sensors in operative communication with the monitoring unit, wherein the monitoring unit uses signals received from both the movement sensors and the sensing unit to determine the presence of a person on the mattress or chair support.

4. The system of claim 1, wherein the monitoring unit is further configured to determine an average static pressure within the fluid or gas-filled pad of the sensing unit and calculate a weight of the subject using the determined average static pressure.

5. The system of 1, wherein said monitoring unit includes a processor operative to (i) generate heart-rate information of the subject, based on time-dependent signals having frequency components in the range from about 0.1 to about 10 Hz, and (ii) generate respiration rate information of the subject based on time-dependent signals having frequency components in the range less than about 1 Hz.

6. The system of claim 1, wherein the first pump and the second pump are the same pump.

7. The system of claim 1, wherein the first pump is distinct from the second pump.

8. A system for monitoring heart and respiration rates of a human subject at rest, comprising, in operative condition:
a sensing unit adapted for use with a mattress, for cushioning at least an upper body portion of a subject lying on or resting against the mattress, the sensing unit including a motion sensor for generating electrical signals in response to motion by movement of the subject, the sensing unit including a fluid or gas-filled pad;
a first pump in fluid or gas communication with the fluid or gas filled pad for maintaining fluid or gas within the pad at a selected pressure or within a defined pressure range;
an ambient-null device comprising an ambient motion sensor for generating electrical signals in response to ambient motion in the vicinity of the subject, the ambient-null device including a fluid or gas-filled ambient pad and a second pump in fluid or gas communication with the fluid or gas-filled ambient pad for filling the fluid or gas-filled ambient pad; and
a monitoring unit operatively connected to the sensing unit and the ambient-null device, the monitoring unit configured to: (i) receive signals from the sensing unit and the ambient-null device, (ii) filter ambient motion indicated by the signals received by the ambient-null device from the signals received from the sensing unit, (iii) generate information about a condition of the subject using the signals received from the sensing unit that have been filtered to remove signals indicative of ambient motion, and (iv) generate an alert or initiate an action based on the information about the condition of the subject.

9. The system of claim 8, wherein the motion sensor of the sensing unit and the ambient motion sensor of the ambient-null device are the same model of sensor.

10. The system of claim 8, wherein the first pump and the second pump are the same pump.

11. The system of claim 8, wherein the first pump is distinct from the second pump.

12. A method of determining heart and respiration rates of a subject, the method comprising:
receiving signals generated by a pressure sensor of a sensing unit for determining pressure fluctuations in a fluid or gas-filled pad of a mattress or chair support, the fluid or gas-filled pad being in fluid or gas communication with a first pump configured to maintain fluid or gas within the fluid or gas-filled pad at a selected pressure or within a defined pressure range;
receiving signals generated by an ambient pressure sensor of an ambient-null device, wherein the ambient pressure sensor generates electrical signals in response to ambient motion in the vicinity of the subject, the ambient-null device including a fluid or gas-filled ambient pad and a second pump in fluid or gas communication with the fluid or gas-filled ambient pad for filling the fluid or gas-filled ambient pad;
filtering ambient motion from pressure variations indicated by signals received from the pressure sensor of the sensing unit by subtracting the electrical signals generated by the ambient pressure sensor from the signals generated by the pressure sensor of the sensing unit;
generating information about the heart and respiration rates of the subject using the signals received from the pressure sensor of the sensing unit that have been filtered to remove the ambient motion; and
relaying such information to a monitoring station or individual.

13. The system of claim 12, wherein the first pump and the second pump are the same pump.

14. The system of claim 12, wherein the first pump is distinct from the second pump.

* * * * *